US005686239A

United States Patent [19]

Reyes et al.

[11] Patent Number: 5,686,239

[45] Date of Patent: Nov. 11, 1997

[54] HEPATITIS E VIRUS PEPTIDES AND METHODS

[75] Inventors: Gregory R. Reyes, Palo Alto; Albert W. Tam, San Francisco, both of Calif.; Patrice O. Yarbough, San Antonio, Tex.

[73] Assignee: Genelabs Technologies, Inc., Redwood City, Calif.

[21] Appl. No.: 240,049

[22] Filed: May 9, 1994

Related U.S. Application Data

[63] Continuation-in-part of Ser. No. 876,941, May 1, 1992, and Ser. No. 870,985, Apr. 20, 1992, each is a continuation-in-part of Ser. No.822,335, Jan. 17, 1992, abandoned, which is a continuation-in-part of Ser. No. 681,078, Apr. 5, 1991, abandoned, which is a continuation-in-part of Ser. No. 505,888, Apr. 5, 1990, abandoned, which is a continuation-in-part of Ser. No. 420,921, Oct. 13, 1989, abandoned, which is a continuation-in-part of Ser. No. 367,486, Jun. 16, 1989, abandoned, which is a continuation-in-part of Ser. No. 336,672, Apr. 11, 1989, abandoned, which is a continuation-in-part of Ser. No. 208,997, Jun. 17, 1988, abandoned.

[51] Int. Cl.[6] .......................... C12Q 1/70; G01N 33/543; C07K 14/005; C07K 17/00

[52] U.S. Cl. ............................. 435/5; 435/975; 436/518; 530/324; 530/403

[58] Field of Search .................................... 530/324, 350, 530/403; 424/189.1, 192.1, 228.1; 435/5, 975; 436/518

[56] References Cited

FOREIGN PATENT DOCUMENTS

| | | |
|---|---|---|
| WO/89/12462 | 12/1989 | WIPO . |
| WO/89/12641 | 12/1989 | WIPO . |
| WO/91/15603 | 10/1991 | WIPO . |
| WO/93/14116 | 7/1993 | WIPO . |
| WO/93/14208 | 7/1993 | WIPO . |
| WO/94/06913 | 3/1994 | WIPO . |

OTHER PUBLICATIONS

Bradley, D.W., et al., "Enterically transmitted non-A, non-B hepatitis: Serial passage of disease in cynomolgus macaques and tamarins and recovery of disease-associated 27-to 34-nm viruslike particles", *Proc. Natl. Acad. Sci. USA* 84(17):6277–81 (1987).

Dawson, G.J., et al., "Solid-phase enzyme-linked immunosorbent assay for hepatitis E virus IgG and IgM antibodies utilizing recombinant antigens and synthetic peptides" *J. Virol. Methods* 38(1):175–86 (1992).

Huang, C.-C., et al., "Molecular Cloning and Sequencing of the Mexico Isolate of Hepatitis E Virus (HEV)", *Virology* 191(2):550–8 (1992).

Kaur, M., et al., "Human linear B-cell epitopes encoded by the hepatitis E virus include determinants in the RNA-dependant RNA polymerase" *Proc. Natl. Acad. Sci. USA* 89 (May):3855–8 (1992).

Khudyakov, Y.E., et al., "Epitope Mapping in Proteins of Hepatitis E Virus", *Virology* 194(4):89–96 (1993).

Lok, A.S.F., et al., "Comparison of Reactivity to ORF 2 and ORF 3 HEV Antigens in IgG and IgM Anti-HEV Assasy", *International Symposium on Viral Hepatitis and Liver Disease* —Scientific Program and Abstract Volume, Abstract 694, p. 262.

Purdy, M.A., et al., "Expression of a hepatitis E virus (HEV)-trpE fusion protein containing epitopes recognized by antibodies in sera from human cases and experimentally infected primates", *Archives of Virology* 123(3–4):335–49 (1992).

(List continued on next page.)

*Primary Examiner*—Mary E. Mosher
*Attorney, Agent, or Firm*—Allan A. Brookes; Charles K. Sholtz; Peter J. Dehlinger

[57] ABSTRACT

Peptide antigens are provided which are derived from the enterically transmitted non-A/non-B viral hepatitis agent, known as hepatitis E virus (HEV). The HEV derived peptides and in particular, SG3, are immunoreactive with sera from individuals infected with HEV. The antigens are useful as diagnostic reagents in diagnostic methods and kits for determining infection of an individual with HEV.

12 Claims, 8 Drawing Sheets

OTHER PUBLICATIONS

Reyes, G.R., et al., "Isolation of a cDNA from the Virus Responsible for Enterically Transmitted Non–A, Non–B Hepatitis", *Science* 247(4948):1335–9 (1990).

Tam, A.W., et al., "Hepatitis E Virus (HEV): Molecular Cloning and Sequencing of the Full–Length Viral Genome" *Virology* 185(1):120–31 (1991).

Tsarev, A., et al., "ELISA for Antibody Hepatitis E Virus (HEV) Based on Complete Open–Reading Frame–2 Protein Expressed in Insect Cells: Identification of HEV Infection in Primates" *J. Infect. Dis.* 168(2):369–78 (1993).

Yarbough, P.O., et al., "Hepatitis E Virus: Identification of Type–Common Epitopes", *J. Virol.* 65(11):5790–7 (1991).

```
      I-ORF3-->                                        I-ORF2-->

     5110v     5120v     5130v     5140v     5150v     5160v
TGGAATGAATAACATGTCTTTTGCTGCGCCCATGGGTTCGCGACCATGCGCCCTCGGCCT
  GAATGAATAACATGT  TTTGCTGCGCCCATGGGTTCGC ACCATGCGCCCT GGCCT
CTGAATGAATAACATGTGGTTTGCTGCGCCCATGGGTTCGCCACCATGCGCCCTAGGCCT

     5170v     5180v     5190v     5200v     5210v     5220v
ATTTTGTTGCTGCTCCTCATGTTTTTGCCTATGCTGCCCGCGCCACCGCCCGGTCAGCCG
 TTTTG TG TG TCCTC TGTTT TGCCTATG TGCCCGCGCCACCG CCGGTCAGCCG
CTTTTGCTGTTGTTCCTCTTGTTTCTGCCTATGTTGCCCGCGCCACCGACCGGTCAGCCG

     5230v     5240v     5250v     5260v     5270v     5280v
TCTGGCCGCCGTCGTGGGCGGCGCAGCGGCGGTTCCGGCGGTGGTTTCTGGGGTGACCGG
TCTGGCCGCCGTCGTGGGCGGCGCAGCGGCGGT CCGGCGGTGGTTTCTGGGGTGACCGG
TCTGGCCGCCGTCGTGGGCGGCGCAGCGGCGGTACCGGCGGTGGTTTCTGGGGTGACCGG

     5290v     5300v     5310v     5320v     5330v     5340v
GTTGATTCTCAGCCCTTCGCAATCCCCTATATTCATCCAACCAACCCCTTCGCCCCCGAT
GTTGATTCTCAGCCCTTCGCAATCCCCTATATTCATCCAACCAACCCCTT GCCCC GA
GTTGATTCTCAGCCCTTCGCAATCCCCTATATTCATCCAACCAACCCCTTTGCCCCAGAC

                                     I-406.4-2-->

     5350v     5360v     5370v     5380v     5390v     5400v
GTCACCGCTGCGGCCGGGGCTGGACCTCGTGTTCGCCAACCCGCCCGACCACTCGGCTCC
GT  CCGCTGCG CCGGG CTGGACCTCG  TTCGCCAACC GCCCG CCACT GGCTCC
GTTGCCGCTGCGTCCGGGTCTGGACCTCGCCTTCGCCAACCAGCCCGGCCACTTGGCTCC

     5410v     5420v     5430v     5440v     5450v     5460v
GCTTGGCGTGACCAGGCCCAGCGCCCCGCCGTTGCCTCACGTCGTAGACCTACCACAGCT
 CTTGGCG GA CAGGCCCAGCGCCCC CCG TGCCTC CGTCG  GACCT CCACAGC
ACTTGGCGAGATCAGGCCCAGCGCCCCTCCGCTGCCTCCCGTCGCCGACCTGCCACAGCC

  <--406.4-2-I
      <-ORF3--I

   5470v     5480v     5490v     5500v     5510v     5520v
GGGGCCGCGCCGCTAACCGCGGTCGCTCCGGCCCATGACACCCCGCCAGTGCCTGATGTC
GGGGC GCG CGCT AC GC GT GC CC GCCCATGACACC C CC GT CC GA GT
GGGGCTGCGGCGCTGACGGCTGTGGCGCCTGCCCATGACACCTCACCCGTCCCGGACGTT

     5530v     5540v     5550v     5560v     5570v     5580v
GACTCCCGCGGCGCCATCTTGCGCCGGCAGTATAACCTATCAACATCTCCCCTTACCTCT
GA TC CGCGG GC AT  T CGCCG CAGTATAA  T TC AC TC CCCCT AC TC
GATTCTCGCGGTGCAATTCTACGCCGCCAGTATAATTTGTCTACTTCACCCCTGACATCC
```

Fig. 2A

```
     5590v     5600v     5610v     5620v     5630v     5640v
TCCGTGGCCACCGGCACTAACCTGGTTCTTTATGCCGCCCCTCTTAGTCCGCTTTTACCC
TC GTGGCC C GGCACTAA  T GT CT TATGC GCCCC CTTA TCCGC T T CC
TCTGTGGCCTCTGGCACTAATTTAGTCCTGTATGCAGCCCCCCTTAATCCGCCTCTGCCG

     5650v     5660v     5670v     5680v     5690v     5700v
CTTCAGGACGGCACCAATACCCATATAATGGCCACGGAAGCTTCTAATTATGCCCAGTAC
CT CAGGACGG AC AATAC CA AT ATGGCCAC GA GC TC AATTATGC CAGTAC
CTGCAGGACGGTACTAATACTCACATTATGGCCACAGAGGCCTCCAATTATGCACAGTAC

     5710v     5720v     5730v     5740v     5750v     5760v
CGGGTTGCCCGTGCCACAATCCGTTACCGCCCGCTGGTCCCCAATGCTGTCGGCGGTTAC
CGGGTTGCCCG GC AC ATCCGTTACCG CC CT GT CC AATGC GT GG GG TA
CGGGTTGCCCGCGCTACTATCCGTTACCGGCCCCTAGTGCCTAATGCAGTTGGAGGCTAT


                                                 (C2) I->

     5770v     5780v     5790v     5800v     5810v     5820v
GCCATCTCCATCTCATTCTGGCCACAGACCACCACCACCCCGACGTCCGTTGATATGAAT
GC AT TCCAT TC TTCTGGCC CA AC ACCAC ACCCC AC TC GTTGA ATGAAT
GCTATATCCATTTCTTTCTGGCCTCAAACAACCACAACCCCTACATCTGTTGACATGAAT

     5830v     5840v     5850v     5860v     5870v     5880v
TCAATAACCTCGACGGATGTTCGTATTTTAGTCCAGCCCGGCATAGCCTCTGAGCTTGTG
TC AT AC TC AC GATGT  G ATT T GT CA CC GGCATAGC TCTGA  T GT
TCCATTACTTCCACTGATGTCAGGATTCTTGTTCAACCTGGCATAGCATCTGAATTGGTC

     5890v     5900v     5910v     5920v     5930v     5940v
ATCCCAAGTGAGCGCCTACACTATCGTAACCAAGGCTGGCGCTCCGTCGAGACCTCTGGG
ATCCCAAG GAGCGCCT CACTA CG AA CAAGG TGGCGCTC GT GAGAC TCTGG
ATCCCAAGCGAGCGCCTTCACTACCGCAATCAAGGTTGGCGCTCGGTTGAGACATCTGGT

     5950v     5960v     5970v     5980v     5990v     6000v
GTGGCTGAGGAGGAGGCTACCTCTGGTCTTGTTATGCTTTGCATACATGGCTCACTCGTA
GT GCTGAGGAGGA GC ACCTC GGTCTTGT ATG T TGCATACATGGCTC C  GT
GTTGCTGAGGAGGAAGCCACCTCCGGTCTTGTCATGTTATGCATACATGGCTCTCCAGTT

     6010v     6020v     6030v     6040v     6050v     6060v
AATTCCTATACTAATACACCCTATACCGGTGCCCTCGGGCTGTTGGACTTTGCCCTTGAG
AA TCCTATAC AATAC CC TATACCGGTGCCCT GG  T  TGGACTTTGCC T GAG
AACTCCTATACCAATACCCCTTATACCGGTGCCCTTGGCTTACTGGACTTTGCCTTAGAG


     6070v     6080v     6090v     6100v     6110v     6120v
CTTGAGTTTCGCAACCTTACCCCCGGTAACACCAATACGCGGGTCTCCCGTTATTCCAGC
CTTGAGTTTCGCAA CT ACC CC GTAACACCAATAC CG GT TCCCGTTA TCCAGC
CTTGAGTTTCGCAATCTCACCACCTGTAACACCAATACACGTGTGTCCCGTTACTCCAGC
```

```
                    I-SG3-->

     6130v     6140v     6150v     6160v     6170v     6180v
ACTGCTCGCCACCGCCTTCGTCGCGGTGCGGACGGGACTGCCGAGCTCACCACCACGGCT
ACTGCTCG CAC  C   CG  G G     GACGGGACTGC GAGCT ACCAC AC GC
ACTGCTCGTCACTCCGCCCGAGGGGCC---GACGGGACTGCGGAGCTGACCACAACTGCA

     6190v     6200v     6210v     6220v     6230v     6240v
GCTACCCGCTTTATGAAGGACCTCTATTTTACTAGTACTAATGGTGTCGGTGAGATCGGC
GC ACC G TT ATGAA GA CTC A TTTAC  G   TAATGG GT GGTGA  TCGGC
GCCACCAGGTTCATGAAAGATCTCCACTTTACCGGCCTTAATGGGGTAGGTGAAGTCGGC

     6250v     6260v     6270v     6280v     6290v     6300v
CGCGGGATAGCCCTCACCCTGTTCAACCTTGCTGACACTCTGCTTGGCGGCCTGCCGACA
CGCGGGATAGC CT AC  T  T AACCTTGCTGACAC CT CT GGCGG CT CCGACA
CGCGGGATAGCTCTAACATTACTTAACCTTGCTGACACGCTCCTCGGCGGGCTCCCGACA

     6310v     6320v     6330v     6340v     6350v     6360v
GAATTGATTTCGTCGGCTGGTGGCCAGCTGTTCTACTCCCGTCCCGTTGTCTCAGCCAAT
GAATT ATTTCGTCGGCTGG GG CA CTGTT TA TCCCG CC GTTGTCTCAGCCAAT
GAATTAATTTCGTCGGCTGGCGGCAACTGTTTTATTCCCGCCCGGTTGTCTCAGCCAAT

     6370v     6380v     6390v     6400v     6410v     6420v
GGCGAGCCGACTGTTAAGTTGTATACATCTGTAGAGAATGCTCAGCAGGATAAGGGTATT
GGCGAGCC AC GT AAG T TATACATC GT GAGAATGCTCAGCAGGATAAGGGT TT
GGCGAGCCAACCGTGAAGCTCTATACATCAGTGGAGAATGCTCAGCAGGATAAGGGTGTT

     6430v     6440v     6450v     6460v     6470v     6480v
GCAATCCCGCATGACATTGACCTCGGAGAATCTCGTGTGGTTATTCAGGATTATGATAAC
GC ATCCC CA GA AT GA CT GG GA TC CGTGTGGT ATTCAGGATTATGA AAC
GCTATCCCCCACGATATCGATCTTGGTGATTCGCGTGTGGTCATTCAGGATTATGACAAC

     6490v     6500v     6510v     6520v     6530v     6540v
CAACATGAACAAGATCGGCCGACGCCTTCTCCAGCCCCATCGCGCCCTTTCTCTGTCCTT
CA CATGA CA GATCGGCC AC CC TC CC GC CCATC CG CCTTT TCTGT CT
CAGCATGAGCAGGATCGGCCCACCCCGTCGCCTGCGCCATCTCGGCCTTTTTCTGTTCTC

     6550v     6560v     6570v     6580v     6590v     6600v
CGAGCTAATGATGTGCTTTGGCTCTCTCTCACCGCTGCCGAGTATGACCAGTCCACTTAT
CGAGC AATGATGT CTTTGGCT TC CTCAC GC GCCGAGTATGACCAGTCCACTTA
CGAGCAAATGATGTACTTTGGCTGTCCCTCACTGCAGCCGAGTATGACCAGTCCACTTAC

     6610v     6620v     6630v     6640v     6650v     6660v
GGCTCTTCGACTGGCCCAGTTTATGTTTCTGACTCTGTGACCTTGGTTAATGTTGCGACC
GG TC TC ACTGGCCC GTTTAT T TC GAC   GTGAC TTGGT AATGTTGCGAC
GGGTCGTCAACTGGCCCGGTTTATATCTCGGACAGCGTGACTTTGGTGAATGTTGCGACT

     6670v     6680v     6690v     6700v     6710v     6720v
GGCGCGCAGGCCGTTGCCCGGTCGCTCGATTGGACCAAGGTCACACTTGACGGTCGCCCC
GGCGCGCAGGCCGT GCCCG TCGCT GA TGG CCAA GTCAC CT GACGG CG CCC
GGCGCGCAGGCCGTAGCCCGATCGCTTGACTGGTCCAAAGTCACCCTCGACGGGCGGCCC
```

Fig. 2C

```
     6730v       6740v       6750v       6760v       6770v       6780v
CTCTCCACCATCCAGCAGTACTCGAAGACCTTCTTTGTCCTGCCGCTCCGCGGTAAGCTC
CTC C AC  T  AGCA TA TC AAGAC TTCTTTGT CT CC CT CG GG AAGCTC
CTCCCGACTGTTGAGCAATATTCCAAGACATTCTTTGTGCTCCCCCTTCGTGGCAAGCTC

     6790v       6800v       6810v       6820v       6830v       6840v
TCTTTCTGGGAGGCAGGCACAACTAAAGCCGGGTACCCTTATAATTATAACACCACTGCT
TC TT TGGGAGGC GGCACAAC AAAGC GG TA CCTTATAATTATAA AC ACTGCT
TCCTTTTGGGAGGCCGGCACAACAAAAGCAGGTTATCCTTATAATTATAATACTACTGCT

     6850v       6860v       6870v       6880v       6890v       6900v
AGCGACCAACTGCTTGTCGAGAATGCCGCCGGGCACCGGGTCGCTATTTCCACTTACACC
AG GACCA  T CT  T GA AATGC GCCGG CA CGGGTCGC ATTTC AC TA ACC
AGTGACCAGATTCTGATTGAAAATGCTGCCGGCCATCGGGTCGCCATTTCAACCTATACC

     6910v       6920v       6930v       6940v       6950v       6960v
ACTAGCCTGGGTGCTGGTCCCGTCTCCATTTCTGCGGTTGCCGTTTTAGCCCCCCACTCT
AC AG CT GG GC GGTCC GTC CCATTTCTGCGG  GC GTTTT GC CC C CTC
ACCAGGCTTGGGGCCGGTCCGGTCGCCATTTCTGCGGCCGCGGTTTTGGCTCCACGCTCC

                       I-406.3-2-->

     6970v       6980v       6990v       7000v       7010v       7020v
GCGCTAGCATTGCTTGAGGATACCTTGGACTACCCTGCCCGCGCCCATACTTTTGATGAT
GC CT GC  TGCT GAGGATAC TT GA TA CC G  CG GC CA AC TTTGATGA
GCCCTGGCTCTGCTGGAGGATACTTTTGATTATCCGGGGCGGGCGCACACATTTGATGAC

     7030v       7040v       7050v       7060v       7070v       7080v
TTCTGCCCAGAGTGCCGCCCCCTTGGCCTTCAGGGCTGCGCTTTCCAGTCTACTGTCGCT
TTCTGCCC GA TGCCGC C  T GGCCT CAGGG TG GCTTTCCAGTC ACTGTCGCT
TTCTGCCCTGAATGCCGCGCTTTAGGCCTCCAGGGTTGTGCTTTCCAGTCAACTGTCGCT

                         <--SG3-I
                      <--406.3-2-I

     7090v       7100v       7110v       7120v       7130v       7140v
GAGCTTCAGCGCCTTAAGATGAAGGTGGGTAAAACTCGGGAGTTGTAGTTTATTTGCTTG
GAGCT CAGCGCCTTAA  T AAGGTGGGTAAAACTCGGGAGTTGTAGTTTATTTG  TG
GAGCTCCAGCGCCTTAAAGTTAAGGTGGGTAAAACTCGGGAGTTGTAGTTTATTTGGCTG

     7150v       7160v                   7170v       7180v       7190v
TGCCCCCCTTCTTTCTGTTGC---------TTATTTCTCATTTCTGCGTTCCGCGCTCCC
TGCCC CCT CTT     TGC         TTATTTC   TTTCT  GT CCGCGCTCCC
TGCCCACCTACTTATATCTGCTGATTTCCTTTATTTCCTTTTTCTCGGTCCCGCGCTCCC

<-I ORF2             <-I trpE-C2

  v 7195
TGA
TGA
TGA
```

Fig. 2D

```
        10        20        30        40        50        60
MNNMSFAAPMGSRPCALGLFCCCSSCFCLCCPRHRPVSRLAAVVGGAAAVPAVVSGVTGL
X::: :::::::.:::::::::::::::::::::::::::::::::::::::::::::::
MNNMWFAAPMGSPPCALGLFCCCSSCFCLCCPRHRPVSRLAAVVGGAAAVPAVVSGVTGL
        10        20        30        40        50        60

               406.4-2
        70        80        90       100       110       120
ILSPSQSPIFIQPTPSPPMSPLRPGLDLVFANPPDHSAPLGVTRPSAPPLPHVVDLPQLG
::::::::::::::: :.  ::::::::.:::.:.: :::: .::::::::.:.:::: :
ILSPSQSPIFIQPTPLPQTLPLRPGLDLAFANQPGHLAPLGEIRPSAPPLPPVADLPQPG
        70        80        90       100       110       120

PRRZ
 ::X
LRRZ
```

Fig. 3

```
        10        20        30        40        50        60
MRPRPILLLLLMFLPMLPAPPPGQPSGRRRGRRSGGSGGGFWGDRVDSQPFAIPYIHPTN
X::::.:::.:.:::::::::.::::::::::::::.:::::::::::::::::::::::
MRPRPLLLLFLLFLPMLPAPPTGQPSGRRRGRRSGGTGGGFWGDRVDSQPFAIPYIHPTN
        10        20        30        40        50        60

        70        80        90       100       110       120
PFAPDVTAAAGAGPRVRQPARPLGSAWRDQAQRPAVASRRRPTTAGAAPLTAVAPAHDTP
::::::.::.:.:::.:::::::::.::::::::..::::::.:::::.::::::::::.
PFAPDVAAASGSGPRLRQPARPLGSTWRDQAQRPSAASRRRPATAGAAALTAVAPAHDTS
        70        80        90       100       110       120

       130       140       150       160       170       180
PVPDVDSRGAILRRQYNLSTSPLTSSVATGTNLVLYAAPLSPLLPLQDGTNTHIMATEAS
::::::::::::::::::::::::::::.:::::::::::.: :::::::::::::::::
PVPDVDSRGAILRRQYNLSTSPLTSSVASGTNLVLYAAPLNPPLPLQDGTNTHIMATEAS
       130       140       150       160       170       180

                                C-2
       190       200       210       220       230       240
NYAQYRVARATIRYRPLVPNAVGGYAISISFWPQTTTTPTSVDMNSITSTDVRILVQPGI
::::::::::::::::::::::::::::::::::::::::::::::::::::::::::::
NYAQYRVARATIRYRPLVPNAVGGYAISISFWPQTTTTPTSVDMNSITSTDVRILVQPGI
       190       200       210       220       230       240

       250       260       270       280       290       300
ASELVIPSERLHYRNQGWRSVETSGVAEEEATSGLVMLCIHGSLVNSYTNTPYTGALGLL
::::::::::::::::::::::::::::::::::::::::::: ::::::::::::::::
ASELVIPSERLHYRNQGWRSVETSGVAEEEATSGLVMLCIHGSPVNSYTNTPYTGALGLL
       250       260       270       280       290       300

                        SG3
       310       320       330       340       350       360
DFALELEFRNLTPGNTNTRVSRYSSTARHRLRRGADGTAELTTTAATRFMKDLYFTSTNG
::::::::::::. :::::::::::::::. ::::::::::::::::::::::.::. ::
DFALELEFRNLTTCNTNTRVSRYSSTARHS-ARGADGTAELTTTAATRFMKDLHFTGLNG
       310       320       330       340       350

       370       380       390       400       410       420
VGEIGRGIALTLFNLADTLLGGLPTELISSAGGQLFYSRPVVSANGEPTVKLYTSVENAQ
:::.::::::::.:::::::::::::::::::::::::::::::::::::::::::::::
VGEVGRGIALTLLNLADTLLGGLPTELISSAGGQLFYSRPVVSANGEPTVKLYTSVENAQ
360        370       380       390       400       410

       430       440       450       460       470       480
QDKGIAIPHDIDLGESRVVIQDYDNQHEQDRPTPSPAPSRPFSVLRANDVLWLSLTAAEY
::::.:::::::::.:::::::::::::::::::::::::::::::::::::::::::::
QDKGVAIPHDIDLGDSRVVIQDYDNQHEQDRPTPSPAPSRPFSVLRANDVLWLSLTAAEY
420        430       440       450       460       470
```

Fig. 4A

```
          490        500        510        520        530        540
   DQSTYGSSTGPVYVSDSVTLVNVATGAQAVARSLDWTKVTLDGRPLSTIQQYSKTFFVLP
   :::::::::::::.::::::::::::::::::::::::::.::::::::::.:..:::::
   DQSTYGSSTGPVYISDSVTLVNVATGAQAVARSLDWSKVTLDGRPLPTVEQYSKTFFVLP
480        490        500        510        520        530

          550        560        570        580        590        600
   LRGKLSFWEAGTTKAGYPYNYNTTASDQLLVENAAGHRVAISTYTTSLGAGPVSISAVAV
   ::::::::::::::::::::::::::::.:.:::::::::::::::.::::::.:::.::
   LRGKLSFWEAGTTKAGYPYNYNTTASDQILIENAAGHRVAISTYTTRLGAGPVAISAAAV
540        550        560        570        580        590

          406.3-2
          610        620        630        640        650

   LAPHSALALLEDTLDYPARAHTFDDFCPECRPLGLQGCAFQSTVAELQRLKMKVGKTRELZ
   :::.:::::::::.:::.:::::::::::::.:::::::::::::::::::.::::::::
   LAPRSALALLEDTFDYPGRAHTFDDFCPECRALGLQGCAFQSTVAELQRLKVKVGKTRELZ
600        610        620        630        640        650
```

Fig. 4B

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:

( A ) LENGTH: 1983 base pairs ( B ) TYPE: nucleic acid

-continued ( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Burma strain)
ORF-2

( x i ) SEQUENCE DESCRIPTION: SEQ ID NO:1:

```
ATGCGCCCTC GGCCTATTTT GTTGCTGCTC CTCATGTTTT TGCCTATGCT GCCCGCGCCA   60
CCGCCCGGTC AGCCGTCTGG CCGCCGTCGT GGGCGGCGCA GCGGCGGTTC CGGCGGTGGT  120
TTCTGGGGTG ACCGGGTTGA TTCTCAGCCC TTCGCAATCC CCTATATTCA TCCAACCAAC  180
CCCTTCGCCC CCGATGTCAC CGCTGCGGCC GGGGCTGGAC CTCGTGTTCG CCAACCCGCC  240
CGACCACTCG GCTCCGCTTG GCGTGACCAG GCCCAGCGCC CCGCCGTTGC CTCACGTCGT  300
AGACCTACCA CAGCTGGGGC CGCGCCGCTA ACCGCGGTCG CTCCGGCCCA TGACACCCCG  360
CCAGTGCCTG ATGTCGACTC CCGCGGCGCC ATCTTGCGCC GGCAGTATAA CCTATCAACA  420
TCTCCCCTTA CCTCTTCCGT GGCCACCGGC ACTAACCTGG TTCTTTATGC CGCCCCTCTT  480
AGTCCGCTTT TACCCCTTCA GGACGGCACC AATACCCATA TAATGGCCAC GGAAGCTTCT  540
AATTATGCCC AGTACCGGGT TGCCCGTGCC ACAATCCGTT ACCGCCCGCT GGTCCCCAAT  600
GCTGTCGGCG GTTACGCCAT CTCCATCTCA TTCTGGCCAC AGACCACCAC CACCCCGACG  660
TCCGTTGATA TGAATTCAAT AACCTCGACG GATGTTCGTA TTTTAGTCCA GCCCGGCATA  720
GCCTCTGAGC TTGTGATCCC AAGTGAGCGC CTACACTATC GTAACCAAGG CTGGCGCTCC  780
GTCGAGACCT CTGGGGTGGC TGAGGAGGAG GCTACCTCTG GTCTTGTTAT GCTTTGCATA  840
CATGGCTCAC TCGTAAATTC CTATACTAAT ACACCCTATA CCGGTGCCCT CGGGCTGTTG  900
GACTTTGCCC TTGAGCTTGA GTTTCGCAAC CTTACCCCCG GTAACACCAA TACGCGGGTC  960
TCCCGTTATT CCAGCACTGC TCGCCACCGC CTTCGTCGCG GTGCGGACGG GACTGCCGAG 1020
CTCACCACCA CGGCTGCTAC CCGCTTTATG AAGGACCTCT ATTTTACTAG TACTAATGGT 1080
GTCGGTGAGA TCGGCCGCGG GATAGCCCTC ACCCTGTTCA ACCTTGCTGA CACTCTGCTT 1140
GGCGGCCTGC CGACAGAATT GATTTCGTCG GCTGGTGGCC AGCTGTTCTA CTCCCGTCCC 1200
GTTGTCTCAG CCAATGGCGA GCCGACTGTT AAGTTGTATA CATCTGTAGA GAATGCTCAG 1260
CAGGATAAGG GTATTGCAAT CCCGCATGAC ATTGACCTCG GAGAATCTCG TGTGGTTATT 1320
CAGGATTATG ATAACCAACA TGAACAAGAT CGGCCGACGC CTTCTCCAGC CCCATCGCGC 1380
CCTTTCTCTG TCCTTCGAGC TAATGATGTG CTTTGGCTCT CTCTCACCGC TGCCGAGTAT 1440
GACCAGTCCA CTTATGGCTC TTCGACTGGC CCAGTTTATG TTTCTGACTC TGTGACCTTG 1500
GTTAATGTTG CGACCGGCGC GCAGGCCGTT GCCCGGTCGC TCGATTGGAC CAAGGTCACA 1560
CTTGACGGTC GCCCCCTCTC CACCATCCAG CAGTACTCGA AGACCTTCTT TGTCCTGCCG 1620
CTCCGCGGTA AGCTCTCTTT CTGGGAGGCA GGCACAACTA AAGCCGGGTA CCCTTATAAT 1680
TATAACACCA CTGCTAGCGA CCAACTGCTT GTCGAGAATG CCGCCGGGCA CCGGGTCGCT 1740
ATTTCCACTT ACACCACTAG CCTGGGTGCT GGTCCCGTCT CCATTTCTGC GGTTGCCGTT 1800
TTAGCCCCCC ACTCTGCGCT AGCATTGCTT GAGGATACCT TGGACTACCC TGCCCGCGCC 1860
CATACTTTTG ATGATTTCTG CCCAGAGTGC CGCCCCCTTG GCCTTCAGGG CTGCGCTTTC 1920
CAGTCTACTG TCGCTGAGCT TCAGCGCCTT AAGATGAAGG TGGGTAAAAC TCGGGAGTTG 1980
TAG                                                               1983
```

-continued ( 2 ) INFORMATION FOR SEQ ID NO:2:

( i ) SEQUENCE CHARACTERISTICS:
( A ) LENGTH: 1980 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Mexico Strain)
ORF-2 region ( x i ) SEQUENCE DESCRIPTION: SEQ ID NO:2:

ATGCGCCCTA GGCCTCTTTT GCTGTTGTTC CTCTTGTTTC TGCCTATGTT GCCCGCGCCA 60
CCGACCGGTC AGCCGTCTGG CCGCCGTCGT GGGCGGCGCA GCGGCGGTAC CGGCGGTGGT 120
TTCTGGGGTG ACCGGGTTGA TTCTCAGCCC TTCGCAATCC CCTATATTCA TCCAACCAAC 180
CCCTTTGCCC CAGACGTTGC CGCTGCGTCC GGGTCTGGAC CTCGCCTTCG CCAACCAGCC 240
CGGCCACTTG GCTCCACTTG GCGAGATCAG GCCCAGCGCC CCTCCGCTGC CTCCCGTCGC 300
CGACCTGCCA CAGCCGGGGC TGCGGCGCTG ACGGCTGTGG CGCCTGCCCA TGACACCTCA 360
CCCGTCCCGG ACGTTGATTC TCGCGGTGCA ATTCTACGCC GCCAGTATAA TTTGTCTACT 420
TCACCCCTGA CATCCTCTGT GGCCTCTGGC ACTAATTTAG TCCTGTATGC AGCCCCCCTT 480
AATCCGCCTC TGCCGCTGCA GGACGGTACT AATACTCACA TTATGGCCAC AGAGGCCTCC 540
AATTATGCAC AGTACCGGGT TGCCCGCGCT ACTATCCGTT ACCGGCCCCT AGTGCCTAAT 600
GCAGTTGGAG GCTATGCTAT ATCCATTTCT TTCTGGCCTC AAACAACCAC AACCCCTACA 660
TCTGTTGACA TGAATTCCAT TACTTCCACT GATGTCAGGA TTCTTGTTCA ACCTGGCATA 720
GCATCTGAAT TGGTCATCCC AAGCGAGCGC CTTCACTACC GCAATCAAGG TTGGCGCTCG 780
GTTGAGACAT CTGGTGTTGC TGAGGAGGAA GCCACCTCCG GTCTTGTCAT GTTATGCATA 840
CATGGCTCTC CAGTTAACTC CTATACCAAT ACCCCTTATA CCGGTGCCCT TGGCTTACTG 900
GACTTTGCCT TAGAGCTTGA GTTTCGCAAT CTCACCACCT GTAACACCAA TACACGTGTG 960
TCCCGTTACT CCAGCACTGC TCGTCACTCC GCCCGAGGGG CCGACGGGAC TGCGGAGCTG 1020
ACCACAACTG CAGCCACCAG GTTCATGAAA GATCTCCACT TTACCGGCCT TAATGGGGTA 1080
GGTGAAGTCG GCCGCGGGAT AGCTCTAACA TTACTTAACC TTGCTGACAC GCTCCTCGGC 1140
GGGCTCCCGA CAGAATTAAT TTCGTCGGCT GGCGGGCAAC TGTTTTATTC CCGCCCGGTT 1200
GTCTCAGCCA ATGGCGAGCC AACCGTGAAG CTCTATACAT CAGTGGAGAA TGCTCAGCAG 1260
GATAAGGGTG TTGCTATCCC CCACGATATC GATCTTGGTG ATTCGCGTGT GGTCATTCAG 1320
GATTATGACA ACCAGCATGA GCAGGATCGG CCCACCCCGT CGCCTGCGCC ATCTCGGCCT 1380
TTTTCTGTTC TCCGAGCAAA TGATGTACTT TGGCTGTCCC TCACTGCAGC CGAGTATGAC 1440
CAGTCCACTT ACGGGTCGTC AACTGGCCCG GTTTATATCT CGGACAGCGT GACTTTGGTG 1500
AATGTTGCGA CTGGCGCGCA GGCCGTAGCC CGATCGCTTG ACTGGTCCAA AGTCACCCTC 1560
GACGGGCGGC CCCTCCCGAC TGTTGAGCAA TATTCCAAGA CATTCTTTGT GCTCCCCCTT 1620
CGTGGCAAGC TCTCCTTTTG GGAGGCCGGC ACAACAAAAG CAGGTTATCC TTATAATTAT 1680
AATACTACTG CTAGTGACCA GATTCTGATT GAAAATGCTG CCGGCCATCG GGTCGCCATT 1740
TCAACCTATA CCACCAGGCT TGGGGCCGGT CCGGTCGCCA TTTCTGCGGC CGCGGTTTTG 1800

-continued

| | | | | | | |
|---|---|---|---|---|---|---|
| GCTCCACGCT | CCGCCCTGGC | TCTGCTGGAG | GATACTTTTG | ATTATCCGGG | GCGGGCGCAC | 1860 |
| ACATTTGATG | ACTTCTGCCC | TGAATGCCGC | GCTTTAGGCC | TCCAGGGTTG | TGCTTTCCAG | 1920 |
| TCAACTGTCG | CTGAGCTCCA | GCGCCTTAAA | GTTAAGGTGG | GTAAAACTCG | GGAGTTGTAG | 1980 |

( 2 ) INFORMATION FOR SEQ ID NO:3:

( i ) SEQUENCE CHARACTERISTICS:
( A ) LENGTH: 372 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Burma Strain) ORF-3 region ( x i ) SEQUENCE DESCRIPTION: SEQ ID NO:3:

| | | | | | | |
|---|---|---|---|---|---|---|
| ATGAATAACA | TGTCTTTTGC | TGCGCCCATG | GGTTCGCGAC | CATGCGCCCT | CGGCCTATTT | 60 |
| TGTTGCTGCT | CCTCATGTTT | TTGCCTATGC | TGCCCGCGCC | ACCGCCCGGT | CAGCCGTCTG | 120 |
| GCCGCCGTCG | TGGGCGGCGC | AGCGGCGGTT | CCGGCGGTGG | TTTCTGGGGT | GACCGGGTTG | 180 |
| ATTCTCAGCC | CTTCGCAATC | CCCTATATTC | ATCCAACCAA | CCCCTTCGCC | CCCGATGTCA | 240 |
| CCGCTGCGGC | CGGGGCTGGA | CCTCGTGTTC | GCCAACCCGC | CCGACCACTC | GGCTCCGCTT | 300 |
| GGCGTGACCA | GGCCCAGCGC | CCCGCCGTTG | CCTCACGTCG | TAGACCTACC | ACAGCTGGGG | 360 |
| CCGCGCCGCT | AA | | | | | 372 |

( 2 ) INFORMATION FOR SEQ ID NO:4:

( i ) SEQUENCE CHARACTERISTICS:
( A ) LENGTH: 372 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Mexico Strain) ORF-3 region ( x i ) SEQUENCE DESCRIPTION: SEQ ID NO:4:

| | | | | | | |
|---|---|---|---|---|---|---|
| ATGAATAACA | TGTGGTTTGC | TGCGCCCATG | GGTTCGCCAC | CATGCGCCCT | AGGCCTCTTT | 60 |
| TGCTGTTGTT | CCTCTTGTTT | CTGCCTATGT | TGCCCGCGCC | ACCGACCGGT | CAGCCGTCTG | 120 |
| GCCGCCGTCG | TGGGCGGCGC | AGCGGCGGTA | CCGGCGGTGG | TTTCTGGGGT | GACCGGGTTG | 180 |
| ATTCTCAGCC | CTTCGCAATC | CCCTATATTC | ATCCAACCAA | CCCCTTTGCC | CCAGACGTTG | 240 |
| CCGCTGCGTC | CGGGTCTGGA | CCTCGCCTTC | GCCAACCAGC | CCGGCCACTT | GGCTCCACTT | 300 |
| GGCGAGATCA | GGCCCAGCGC | CCCTCCGCTG | CCTCCCGTCG | CCGACCTGCC | ACAGCCGGGG | 360 |
| CTGCGGCGCT | GA | | | | | 372 |

( 2 ) INFORMATION FOR SEQ ID NO:5:

( i ) SEQUENCE CHARACTERISTICS:
( A ) LENGTH: 126 base pairs
( B ) TYPE: nucleic acid
( C ) STRANDEDNESS: double
( D ) TOPOLOGY: linear -continued ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Burma strain) 406.3- 2

( x i ) SEQUENCE DESCRIPTION: SEQ ID NO:5:

ACCTTGGACT ACCCTGCCCG CGCCCATACT TTTGATGATT TCTGCCCAGA GTGCCGCCCC 60
CTTGGCCTTC AGGGCTGCGC TTTCCAGTCT ACTGTCGCTG AGCTTCAGCG CCTTAAGATG 120
AAGGTG 126

( 2 ) INFORMATION FOR SEQ ID NO:6:

( i ) SEQUENCE CHARACTERISTICS:
( A ) LENGTH: 126 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Mexico strain) 406.3- 2

( x i ) SEQUENCE DESCRIPTION: SEQ ID NO:6:

ACTTTTGATT ATCCGGGGCG GGCGCACACA TTTGATGACT TCTGCCCTGA ATGCCGCGCT 60
TTAGGCCTCC AGGGTTGTGC TTTCCAGTCA ACTGTCGCTG AGCTCCAGCG CCTTAAAGTT 120
AAGGTG 126

( 2 ) INFORMATION FOR SEQ ID NO:7:

( i ) SEQUENCE CHARACTERISTICS:
( A ) LENGTH: 984 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Burma strain) SG3

( x i ) SEQUENCE DESCRIPTION: SEQ ID NO:7:

GGTGCGGACG GGACTGCCGA GCTCACCACC ACGGCTGCTA CCCGCTTTAT GAAGGACCTC 60
TATTTTACTA GTACTAATGG TGTCGGTGAG ATCGGCCGCG GGATAGCCCT CACCCTGTTC 120
AACCTTGCTG ACACTCTGCT TGGCGGCCTG CCGACAGAAT TGATTTCGTC GGCTGGTGGC 180
CAGCTGTTCT ACTCCCGTCC CGTTGTCTCA GCCAATGGCG AGCCGACTGT TAAGTTGTAT 240
ACATCTGTAG AGAATGCTCA GCAGGATAAG GGTATTGCAA TCCCGCATGA CATTGACCTC 300
GGAGAATCTC GTGTGGTTAT TCAGGATTAT GATAACCAAC ATGAACAAGA TCGGCCGACG 360
CCTTCTCCAG CCCCATCGCG CCCTTTCTCT GTCCTTCGAG CTAATGATGT GCTTTGGCTC 420
TCTCTCACCG CTGCCGAGTA TGACCAGTCC ACTTATGGCT CTTCGACTGG CCCAGTTTAT 480
GTTTCTGACT CTGTGACCTT GGTTAATGTT GCGACCGGCG CGCAGGCCGT TGCCCGGTCG 540
CTCGATTGGA CCAAGGTCAC ACTTGACGGT CGCCCCCTCT CCACCATCCA GCAGTACTCG 600

-continued

```
AAGACCTTCT TTGTCCTGCC GCTCCGCGGT AAGCTCTCTT TCTGGGAGGC AGGCACAACT    660
AAAGCCGGGT ACCCTTATAA TTATAACACC ACTGCTAGCG ACCAACTGCT TGTCGAGAAT    720
GCCGCCGGGC ACCGGGTCGC TATTTCCACT TACACCACTA GCCTGGGTGC TGGTCCCGTC    780
TCCATTTCTG CGGTTGCCGT TTTAGCCCCC CACTCTGCGC TAGCATTGCT TGAGGATACC    840
TTGGACTACC CTGCCCGCGC CCATACTTTT GATGATTTCT GCCCAGAGTG CCGCCCCCTT    900
GGCCTTCAGG GCTGCGCTTT CCAGTCTACT GTCGCTGAGC TTCAGCGCCT TAAGATGAAG    960
GTGGGTAAAA CTCGGGAGTT GTAG                                           984
```

( 2 ) INFORMATION FOR SEQ ID NO:8:

( i ) SEQUENCE CHARACTERISTICS:
( A ) LENGTH: 984 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatits E Virus (Mexico strain) SG3

( x i ) SEQUENCE DESCRIPTION: SEQ ID NO:8:

```
GGGGCCGACG GGACTGCGGA GCTGACCACA ACTGCAGCCA CCAGGTTCAT GAAAGATCTC     60
CACTTTACCG GCCTTAATGG GGTAGGTGAA GTCGGCCGCG GGATAGCTCT AACATTACTT    120
AACCTTGCTG ACACGCTCCT CGGCGGGCTC CCGACAGAAT TAATTTCGTC GGCTGGCGGG    180
CAACTGTTTT ATTCCCGCCC GGTTGTCTCA GCCAATGGCG AGCCAACCGT GAAGCTCTAT    240
ACATCAGTGG AGAATGCTCA GCAGGATAAG GGTGTTGCTA TCCCCCACGA TATCGATCTT    300
GGTGATTCGC GTGTGGTCAT TCAGGATTAT GACAACCAGC ATGAGCAGGA TCGGCCCACC    360
CCGTCGCCTG CGCCATCTCG GCCTTTTTCT GTTCTCCGAG CAAATGATGT ACTTTGGCTG    420
TCCCTCACTG CAGCCGAGTA TGACCAGTCC ACTTACGGGT CGTCAACTGG CCCGGTTTAT    480
ATCTCGGACA GCGTGACTTT GGTGAATGTT GCGACTGGCG CGCAGGCCGT AGCCCGATCG    540
CTTGACTGGT CCAAAGTCAC CCTCGACGGG CGGCCCCTCC CGACTGTTGA GCAATATTCC    600
AAGACATTCT TTGTGCTCCC CCTTCGTGGC AAGCTCTCCT TTTGGGAGGC CGGCACAACA    660
AAAGCAGGTT ATCCTTATAA TTATAATACT ACTGCTAGTG ACCAGATTCT GATTGAAAAT    720
GCTGCCGGCC ATCGGGTCGC CATTTCAACC TATACCACCA GGCTTGGGGC CGGTCCGGTC    780
GCCATTTCTG CGGCCGCGGT TTTGGCTCCA CGCTCCGCCC TGGCTCTGCT GGAGGATACT    840
TTTGATTATC CGGGGCGGGC GCACACATTT GATGACTTCT GCCCTGAATG CCGCGCTTTA    900
GGCCTCCAGG GTTGTGCTTT CCAGTCAACT GTCGCTGAGC TCCAGCGCCT TAAAGTTAAG    960
GTGGGTAAAA CTCGGGAGTT GTAG                                           984
```

( 2 ) INFORMATION FOR SEQ ID NO:9:

( i ) SEQUENCE CHARACTERISTICS:
( A ) LENGTH: 99 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:

( C ) INDIVIDUAL ISOLATE: Hepatitis E Virus (Burma strain)
406.4-2 region ( x i ) SEQUENCE DESCRIPTION: SEQ ID NO:9:

```
GCCAACCCGC CCGACCACTC GGCTCCGCTT GGCGTGACCA GGCCCAGCGC CCCGCCGTTG    60
CCTCACGTCG TAGACCTACC ACAGCTGGGG CCGCGCCGC                           99
```

( 2 ) INFORMATION FOR SEQ ID NO:10:

( i ) SEQUENCE CHARACTERISTICS:
( A ) LENGTH: 99 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( C ) INDIVIDUAL ISOLATE: Hepatitis E Virus (Mexico strain)
406.4-2 region ( x i ) SEQUENCE DESCRIPTION: SEQ ID NO:10:

```
GCCAACCAGC CCGGCCACTT GGCTCCACTT GGCGAGATCA GGCCCAGCGC CCCTCCGCTG    60
CCTCCCGTCG CCGACCTGCC ACAGCCGGGG CTGCGGCGC                           99
```

( 2 ) INFORMATION FOR SEQ ID NO:11:

( i ) SEQUENCE CHARACTERISTICS:
( A ) LENGTH: 42 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Burma strain)
406.3- 2

( x i ) SEQUENCE DESCRIPTION: SEQ ID NO:11:

```
Thr Leu Asp Tyr Pro Ala Arg Ala His Thr Phe Asp Asp Phe Cys Pro
1               5                   10                  15

Glu Cys Arg Pro Leu Gly Leu Gln Gly Cys Ala Phe Gln Ser Thr Val
            20                  25                  30

Ala Glu Leu Gln Arg Leu Lys Met Lys Val
        35                  40
```

( 2 ) INFORMATION FOR SEQ ID NO:12:

( i ) SEQUENCE CHARACTERISTICS:
( A ) LENGTH: 42 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Mexico strain)
406.3-2 region ( x i ) SEQUENCE DESCRIPTION: SEQ ID NO:12:

```
Thr Phe Asp Tyr Pro Gly Arg Ala His Thr Phe Asp Asp Phe Cys Pro
1               5                   10                  15
```

-continued

Glu Cys Arg Ala Leu Gly Leu Gln Gly Cys Ala Phe Gln Ser Thr Val
20 25 30

Ala Glu Leu Gln Arg Leu Lys Val Lys Val
35 40

( 2 ) INFORMATION FOR SEQ ID NO:13:

( i ) SEQUENCE CHARACTERISTICS:
( A ) LENGTH: 327 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Burma strain) SG3 region ( x i ) SEQUENCE DESCRIPTION: SEQ ID NO:13:

Gly Ala Asp Gly Thr Ala Glu Leu Thr Thr Thr Ala Ala Thr Arg Phe
1 5 10 15

Met Lys Asp Leu Tyr Phe Thr Ser Thr Asn Gly Val Gly Glu Ile Gly
20 25 30

Arg Gly Ile Ala Leu Thr Leu Phe Asn Leu Ala Asp Thr Leu Leu Gly
35 40 45

Gly Leu Pro Thr Glu Leu Ile Ser Ser Ala Gly Gly Gln Leu Phe Tyr
50 55 60

Ser Arg Pro Val Val Ser Ala Asn Gly Glu Pro Thr Val Lys Leu Tyr
65 70 75 80

Thr Ser Val Glu Asn Ala Gln Gln Asp Lys Gly Ile Ala Ile Pro His
85 90 95

Asp Ile Asp Leu Gly Glu Ser Arg Val Val Ile Gln Asp Tyr Asp Asn
100 105 110

Gln His Glu Gln Asp Arg Pro Thr Pro Ser Pro Ala Pro Ser Arg Pro
115 120 125

Phe Ser Val Leu Arg Ala Asn Asp Val Leu Trp Leu Ser Leu Thr Ala
130 135 140

Ala Glu Tyr Asp Gln Ser Thr Tyr Gly Ser Ser Thr Gly Pro Val Tyr
145 150 155 160

Val Ser Asp Ser Val Thr Leu Val Asn Val Ala Thr Gly Ala Gln Ala
165 170 175

Val Ala Arg Ser Leu Asp Trp Thr Lys Val Thr Leu Asp Gly Arg Pro
180 185 190

Leu Ser Thr Ile Gln Gln Tyr Ser Lys Thr Phe Phe Val Leu Pro Leu
195 200 205

Arg Gly Lys Leu Ser Phe Trp Glu Ala Gly Thr Thr Lys Ala Gly Tyr
210 215 220

Pro Tyr Asn Tyr Asn Thr Thr Ala Ser Asp Gln Leu Leu Val Glu Asn
225 230 235 240

Ala Ala Gly His Arg Val Ala Ile Ser Thr Tyr Thr Thr Ser Leu Gly
245 250 255

Ala Gly Pro Val Ser Ile Ser Ala Val Ala Val Leu Ala Pro His Ser
260 265 270

Ala Leu Ala Leu Leu Glu Asp Thr Leu Asp Tyr Pro Ala Arg Ala His
275 280 285

Thr Phe Asp Asp Phe Cys Pro Glu Cys Arg Pro Leu Gly Leu Gln Gly
290 295 300

-continued

Cys Ala Phe Gln Ser Thr Val Ala Glu Leu Gln Arg Leu Lys Met Lys
305 310 315 320

Val Gly Lys Thr Arg Glu Leu
325

( 2 ) INFORMATION FOR SEQ ID NO:14:

( i ) SEQUENCE CHARACTERISTICS:
( A ) LENGTH: 327 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Mexico strain)
SG3 region ( x i ) SEQUENCE DESCRIPTION: SEQ ID NO:14:

Gly Ala Asp Gly Thr Ala Glu Leu Thr Thr Thr Ala Ala Thr Arg Phe
1 5 10 15

Met Lys Asp Leu His Phe Thr Gly Leu Asn Gly Val Gly Glu Val Gly
20 25 30

Arg Gly Ile Ala Leu Thr Leu Leu Asn Leu Ala Asp Thr Leu Leu Gly
35 40 45

Gly Leu Pro Thr Glu Leu Ile Ser Ser Ala Gly Gly Gln Leu Phe Tyr
50 55 60

Ser Arg Pro Val Val Ser Ala Asn Gly Glu Pro Thr Val Lys Leu Tyr
65 70 75 80

Thr Ser Val Glu Asn Ala Gln Gln Asp Lys Gly Val Ala Ile Pro His
85 90 95

Asp Ile Asp Leu Gly Asp Ser Arg Val Val Ile Gln Asp Tyr Asp Asn
100 105 110

Gln His Glu Gln Asp Arg Pro Thr Pro Ser Pro Ala Pro Ser Arg Pro
115 120 125

Phe Ser Val Leu Arg Ala Asn Asp Val Leu Trp Leu Ser Leu Thr Ala
130 135 140

Ala Glu Tyr Asp Gln Ser Thr Tyr Gly Ser Ser Thr Gly Pro Val Tyr
145 150 155 160

Ile Ser Asp Ser Val Thr Leu Val Asn Val Ala Thr Gly Ala Gln Ala
165 170 175

Val Ala Arg Ser Leu Asp Trp Ser Lys Val Thr Leu Asp Gly Arg Pro
180 185 190

Leu Pro Thr Val Glu Gln Tyr Ser Lys Thr Phe Phe Val Leu Pro Leu
195 200 205

Arg Gly Lys Leu Ser Phe Trp Glu Ala Gly Thr Thr Lys Ala Gly Tyr
210 215 220

Pro Tyr Asn Tyr Asn Thr Thr Ala Ser Asp Gln Ile Leu Ile Glu Asn
225 230 235 240

Ala Ala Gly His Arg Val Ala Ile Ser Thr Tyr Thr Thr Arg Leu Gly
245 250 255

Ala Gly Pro Val Ala Ile Ser Ala Ala Ala Val Leu Ala Pro Arg Ser
260 265 270

Ala Leu Ala Leu Leu Glu Asp Thr Phe Asp Tyr Pro Gly Arg Ala His
275 280 285

Thr Phe Asp Asp Phe Cys Pro Glu Cys Arg Ala Leu Gly Leu Gln Gly

-continued

```
        290                                     295                                     300

Cys Ala Phe Gln Ser Thr Val Ala Glu Leu Gln Arg Leu Lys Val Lys
305                 310                 315                 320

Val Gly Lys Thr Arg Glu Leu
                325
```

( 2 ) INFORMATION FOR SEQ ID NO:15:

( i ) SEQUENCE CHARACTERISTICS:
( A ) LENGTH: 660 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Burma strain) ORF-2

( x i ) SEQUENCE DESCRIPTION: SEQ ID NO:15:

```
Met Arg Pro Arg Pro Ile Leu Leu Leu Leu Leu Met Phe Leu Pro Met
1               5                   10                  15

Leu Pro Ala Pro Pro Pro Gly Gln Pro Ser Gly Arg Arg Arg Gly Arg
            20                  25                  30

Arg Ser Gly Gly Ser Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Glu Ala Thr
            260                 265                 270

Ser Gly Leu Val Met Leu Cys Ile His Gly Ser Leu Val Asn Ser Tyr
        275                 280                 285
```

-continued

Thr Asn Thr Pro Tyr Thr Gly Ala Leu Gly Leu Leu Asp Phe Ala Leu
290 295 300

Glu Leu Glu Phe Arg Asn Leu Thr Pro Gly Asn Thr Asn Thr Arg Val
305 310 315 320

Ser Arg Tyr Ser Ser Thr Ala Arg His Arg Leu Arg Arg Gly Ala Asp
325 330 335

Gly Thr Ala Glu Leu Thr Thr Thr Ala Ala Thr Arg Phe Met Lys Asp
340 345 350

Leu Tyr Phe Thr Ser Thr Asn Gly Val Gly Glu Ile Gly Arg Gly Ile
355 360 365

Ala Leu Thr Leu Phe Asn Leu Ala Asp Thr Leu Leu Gly Gly Leu Pro
370 375 380

Thr Glu Leu Ile Ser Ser Ala Gly Gly Gln Leu Phe Tyr Ser Arg Pro
385 390 395 400

Val Val Ser Ala Asn Gly Glu Pro Thr Val Lys Leu Tyr Thr Ser Val
405 410 415

Glu Asn Ala Gln Gln Asp Lys Gly Ile Ala Ile Pro His Asp Ile Asp
420 425 430

Leu Gly Glu Ser Arg Val Val Ile Gln Asp Tyr Asp Asn Gln His Glu
435 440 445

Gln Asp Arg Pro Thr Pro Ser Pro Ala Pro Ser Arg Pro Phe Ser Val
450 455 460

Leu Arg Ala Asn Asp Val Leu Trp Leu Ser Leu Thr Ala Ala Glu Tyr
465 470 475 480

Asp Gln Ser Thr Tyr Gly Ser Ser Thr Gly Pro Val Tyr Val Ser Asp
485 490 495

Ser Val Thr Leu Val Asn Val Ala Thr Gly Ala Gln Ala Val Ala Arg
500 505 510

Ser Leu Asp Trp Thr Lys Val Thr Leu Asp Gly Arg Pro Leu Ser Thr
515 520 525

Ile Gln Gln Tyr Ser Lys Thr Phe Phe Val Leu Pro Leu Arg Gly Lys
530 535 540

Leu Ser Phe Trp Glu Ala Gly Thr Thr Lys Ala Gly Tyr Pro Tyr Asn
545 550 555 560

Tyr Asn Thr Thr Ala Ser Asp Gln Leu Leu Val Glu Asn Ala Ala Gly
565 570 575

His Arg Val Ala Ile Ser Thr Tyr Thr Thr Ser Leu Gly Ala Gly Pro
580 585 590

Val Ser Ile Ser Ala Val Ala Val Leu Ala Pro His Ser Ala Leu Ala
595 600 605

Leu Leu Glu Asp Thr Leu Asp Tyr Pro Ala Arg Ala His Thr Phe Asp
610 615 620

Asp Phe Cys Pro Glu Cys Arg Pro Leu Gly Leu Gln Gly Cys Ala Phe
625 630 635 640

Gln Ser Thr Val Ala Glu Leu Gln Arg Leu Lys Met Lys Val Gly Lys
645 650 655

Thr Arg Glu Leu
660

( 2 ) INFORMATION FOR SEQ ID NO:16:

( i ) SEQUENCE CHARACTERISTICS:
( A ) LENGTH: 659 amino acids
( B ) TYPE: amino acid
( D ) TOPOLOGY: linear -continued ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Mexico Strain)
ORF-2

( x i ) SEQUENCE DESCRIPTION: SEQ ID NO:16:

| | | | | | | | | | | | | | | | |
|---|---|---|---|---|---|---|---|---|---|---|---|---|---|---|---|
| Met | Arg | Pro | Arg | Pro | Leu | Leu | Leu | Leu | Phe | Leu | Leu | Phe | Leu | Pro | Met |
| 1 | | | | 5 | | | | | 10 | | | | | 15 | |
| Leu | Pro | Ala | Pro | Pro | Thr | Gly | Gln | Pro | Ser | Gly | Arg | Arg | Arg | Gly | Arg |
| | | | 20 | | | | | 25 | | | | | 30 | | |
| Arg | Ser | Gly | Gly | Thr | Gly | Gly | Gly | Phe | Trp | Gly | Asp | Arg | Val | Asp | Ser |
| | | 35 | | | | | 40 | | | | | 45 | | | |
| Gln | Pro | Phe | Ala | Ile | Pro | Tyr | Ile | His | Pro | Thr | Asn | Pro | Phe | Ala | Pro |
| | 50 | | | | | 55 | | | | | 60 | | | | |
| Asp | Val | Ala | Ala | Ala | Ser | Gly | Ser | Gly | Pro | Arg | Leu | Arg | Gln | Pro | Ala |
| 65 | | | | | 70 | | | | | 75 | | | | | 80 |
| Arg | Pro | Leu | Gly | Ser | Thr | Trp | Arg | Asp | Gln | Ala | Gln | Arg | Pro | Ser | Ala |
| | | | | 85 | | | | | 90 | | | | | 95 | |
| Ala | Ser | Arg | Arg | Arg | Pro | Ala | Thr | Ala | Gly | Ala | Ala | Ala | Leu | Thr | Ala |
| | | | 100 | | | | | 105 | | | | | 110 | | |
| Val | Ala | Pro | Ala | His | Asp | Thr | Ser | Pro | Val | Pro | Asp | Val | Asp | Ser | Arg |
| | | 115 | | | | | 120 | | | | | 125 | | | |
| Gly | Ala | Ile | Leu | Arg | Arg | Gln | Tyr | Asn | Leu | Ser | Thr | Ser | Pro | Leu | Thr |
| | 130 | | | | | 135 | | | | | 140 | | | | |
| Ser | Ser | Val | Ala | Ser | Gly | Thr | Asn | Leu | Val | Leu | Tyr | Ala | Ala | Pro | Leu |
| 145 | | | | | 150 | | | | | 155 | | | | | 160 |
| Asn | Pro | Pro | Leu | Pro | Leu | Gln | Asp | Gly | Thr | Asn | Thr | His | Ile | Met | Ala |
| | | | | 165 | | | | | 170 | | | | | 175 | |
| Thr | Glu | Ala | Ser | Asn | Tyr | Ala | Gln | Tyr | Arg | Val | Ala | Arg | Ala | Thr | Ile |
| | | | 180 | | | | | 185 | | | | | 190 | | |
| Arg | Tyr | Arg | Pro | Leu | Val | Pro | Asn | Ala | Val | Gly | Gly | Tyr | Ala | Ile | Ser |
| | | 195 | | | | | 200 | | | | | 205 | | | |
| Ile | Ser | Phe | Trp | Pro | Gln | Thr | Thr | Thr | Thr | Pro | Thr | Ser | Val | Asp | Met |
| | 210 | | | | | 215 | | | | | 220 | | | | |
| Asn | Ser | Ile | Thr | Ser | Thr | Asp | Val | Arg | Ile | Leu | Val | Gln | Pro | Gly | Ile |
| 225 | | | | | 230 | | | | | 235 | | | | | 240 |
| Ala | Ser | Glu | Leu | Val | Ile | Pro | Ser | Glu | Arg | Leu | His | Tyr | Arg | Asn | Gln |
| | | | | 245 | | | | | 250 | | | | | 255 | |
| Gly | Trp | Arg | Ser | Val | Glu | Thr | Ser | Gly | Val | Ala | Glu | Glu | Glu | Ala | Thr |
| | | | 260 | | | | | 265 | | | | | 270 | | |
| Ser | Gly | Leu | Val | Met | Leu | Cys | Ile | His | Gly | Ser | Pro | Val | Asn | Ser | Tyr |
| | | 275 | | | | | 280 | | | | | 285 | | | |
| Thr | Asn | Thr | Pro | Tyr | Thr | Gly | Ala | Leu | Gly | Leu | Leu | Asp | Phe | Ala | Leu |
| | 290 | | | | | 295 | | | | | 300 | | | | |
| Glu | Leu | Glu | Phe | Arg | Asn | Leu | Thr | Thr | Cys | Asn | Thr | Asn | Thr | Arg | Val |
| 305 | | | | | 310 | | | | | 315 | | | | | 320 |
| Ser | Arg | Tyr | Ser | Ser | Thr | Ala | Arg | His | Ser | Ala | Arg | Gly | Ala | Asp | Gly |
| | | | | 325 | | | | | 330 | | | | | 335 | |
| Thr | Ala | Glu | Leu | Thr | Thr | Thr | Ala | Ala | Thr | Arg | Phe | Met | Lys | Asp | Leu |
| | | | 340 | | | | | 345 | | | | | 350 | | |
| His | Phe | Thr | Gly | Leu | Asn | Gly | Val | Gly | Glu | Val | Gly | Arg | Gly | Ile | Ala |
| | | 355 | | | | | 360 | | | | | 365 | | | |
| Leu | Thr | Leu | Leu | Asn | Leu | Ala | Asp | Thr | Leu | Leu | Gly | Gly | Leu | Pro | Thr |

-continued 370 375 380

Glu Leu Ile Ser Ser Ala Gly Gly Gln Leu Phe Tyr Ser Arg Pro Val
385 390 395 400

Val Ser Ala Asn Gly Glu Pro Thr Val Lys Leu Tyr Thr Ser Val Glu
405 410 415

Asn Ala Gln Gln Asp Lys Gly Val Ala Ile Pro His Asp Ile Asp Leu
420 425 430

Gly Asp Ser Arg Val Val Ile Gln Asp Tyr Asp Asn Gln His Glu Gln
435 440 445

Asp Arg Pro Thr Pro Ser Pro Ala Pro Ser Arg Pro Phe Ser Val Leu
450 455 460

Arg Ala Asn Asp Val Leu Trp Leu Ser Leu Thr Ala Ala Glu Tyr Asp
465 470 475 480

Gln Ser Thr Tyr Gly Ser Ser Thr Gly Pro Val Tyr Ile Ser Asp Ser
485 490 495

Val Thr Leu Val Asn Val Ala Thr Gly Ala Gln Ala Val Ala Arg Ser
500 505 510

Leu Asp Trp Ser Lys Val Thr Leu Asp Gly Arg Pro Leu Pro Thr Val
515 520 525

Glu Gln Tyr Ser Lys Thr Phe Phe Val Leu Pro Leu Arg Gly Lys Leu
530 535 540

Ser Phe Trp Glu Ala Gly Thr Thr Lys Ala Gly Tyr Pro Tyr Asn Tyr
545 550 555 560

Asn Thr Thr Ala Ser Asp Gln Ile Leu Ile Glu Asn Ala Ala Gly His
565 570 575

Arg Val Ala Ile Ser Thr Tyr Thr Thr Arg Leu Gly Ala Gly Pro Val
580 585 590

Ala Ile Ser Ala Ala Ala Val Leu Ala Pro Arg Ser Ala Leu Ala Leu
595 600 605

Leu Glu Asp Thr Phe Asp Tyr Pro Gly Arg Ala His Thr Phe Asp Asp
610 615 620

Phe Cys Pro Glu Cys Arg Ala Leu Gly Leu Gln Gly Cys Ala Phe Gln
625 630 635 640

Ser Thr Val Ala Glu Leu Gln Arg Leu Lys Val Lys Val Gly Lys Thr
645 650 655

Arg Glu Leu ( 2 ) INFORMATION FOR SEQ ID NO:17:

( i ) SEQUENCE CHARACTERISTICS:
( A ) LENGTH: 33 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Burma strain) 406.4- 2

( x i ) SEQUENCE DESCRIPTION: SEQ ID NO:17:

Ala Asn Pro Pro Asp His Ser Ala Pro Leu Gly Val Thr Arg Pro Ser
1 5 10 15

Ala Pro Pro Leu Pro His Val Val Asp Leu Pro Gln Leu Gly Pro Arg
20 25 30

Arg ( 2 ) INFORMATION FOR SEQ ID NO:18:

( i ) SEQUENCE CHARACTERISTICS:
( A ) LENGTH: 33 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Mexico strain)
406.4- 2

( x i ) SEQUENCE DESCRIPTION: SEQ ID NO:18:

Ala Asn Gln Pro Gly His Leu Ala Pro Leu Gly Glu Ile Arg Pro Ser
1 5 10 15

Ala Pro Pro Leu Pro Pro Val Ala Asp Leu Pro Gln Pro Gly Leu Arg
20 25 30

Arg ( 2 ) INFORMATION FOR SEQ ID NO:19:

( i ) SEQUENCE CHARACTERISTICS:
( A ) LENGTH: 124 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Burma Strain)
ORF-3

( x i ) SEQUENCE DESCRIPTION: SEQ ID NO:19:

Met Asn Asn Met Ser Phe Ala Ala Pro Met Gly Ser Arg Pro Cys Ala
1 5 10 15

Leu Gly Leu Phe Cys Cys Cys Ser Ser Cys Phe Cys Leu Cys Cys Pro
20 25 30

Arg His Arg Pro Val Ser Arg Leu Ala Ala Val Val Gly Gly Ala Ala
35 40 45

Ala Val Pro Ala Val Val Ser Gly Val Thr Gly Leu Ile Leu Ser Pro
50 55 60

Ser Gln Ser Pro Ile Phe Ile Gln Pro Thr Pro Ser Pro Pro Met Ser
65 70 75 80

Pro Leu Arg Pro Gly Leu Asp Leu Val Phe Ala Asn Pro Pro Asp His
85 90 95

Ser Ala Pro Leu Gly Val Thr Arg Pro Ser Ala Pro Pro Leu Pro His
100 105 110

Val Val Asp Leu Pro Gln Leu Gly Pro Arg Arg Glx
115 120

( 2 ) INFORMATION FOR SEQ ID NO:20:

( i ) SEQUENCE CHARACTERISTICS:
( A ) LENGTH: 124 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: Hepatitis E Virus (Mexico Strain) ORF-3

( x i ) SEQUENCE DESCRIPTION: SEQ ID NO:20:

Met Asn Asn Met Trp Phe Ala Ala Pro Met Gly Ser Pro Pro Cys Ala
1 5 10 15

Leu Gly Leu Phe Cys Cys Cys Ser Ser Cys Phe Cys Leu Cys Cys Pro
20 25 30

Arg His Arg Pro Val Ser Arg Leu Ala Ala Val Val Gly Gly Ala Ala
35 40 45

Ala Val Pro Ala Val Val Ser Gly Val Thr Gly Leu Ile Leu Ser Pro
50 55 60

Ser Gln Ser Pro Ile Phe Ile Gln Pro Thr Pro Leu Pro Gln Thr Leu
65 70 75 80

Pro Leu Arg Pro Gly Leu Asp Leu Ala Phe Ala Asn Gln Pro Gly His
85 90 95

Leu Ala Pro Leu Gly Glu Ile Arg Pro Ser Ala Pro Pro Leu Pro Pro
100 105 110

Val Ala Asp Leu Pro Gln Pro Gly Leu Arg Arg Glx
115 120

( 2 ) INFORMATION FOR SEQ ID NO:21:

( i ) SEQUENCE CHARACTERISTICS:
( A ) LENGTH: 33 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: 406.4-2 consensus sequence ( i x ) FEATURE:
( A ) NAME/KEY: Modified-site
( B ) LOCATION: 3
( D ) OTHER INFORMATION: /note="where Xaa is Q or P"

( i x ) FEATURE:
( A ) NAME/KEY: Modified-site
( B ) LOCATION: 5
( D ) OTHER INFORMATION: /note="where Xaa is G or D"

( i x ) FEATURE:
( A ) NAME/KEY: Modified-site
( B ) LOCATION: 7
( C ) OTHER INFORMATION: /note="where Xaa is L or S"

( i x ) FEATURE:
( A ) NAME/KEY: Modified-site
( B ) LOCATION: 12
( C ) OTHER INFORMATION: /note="where Xaa is E or V"

( i x ) FEATURE:
( A ) NAME/KEY: Modified-site
( B ) LOCATION: 13
( C ) OTHER INFORMATION: /note="where Xaa is I or T"

( i x ) FEATURE:
( A ) NAME/KEY: Modified-site
( B ) LOCATION: 22
( C ) OTHER INFORMATION: /note="where Xaa is P or H"

( i x ) FEATURE:
( A ) NAME/KEY: Modified-site
( B ) LOCATION: 24
( C ) OTHER INFORMATION: /note="where Xaa is A or V"

-continued ( i x ) FEATURE:
( A ) NAME/KEY: Modified-site
( B ) LOCATION: 29
( C ) OTHER INFORMATION: /note="where Xaa is P or L"

( i x ) FEATURE:
( A ) NAME/KEY: Modified-site
( B ) LOCATION: 31
( C ) OTHER INFORMATION: /note="where Xaa is L or P"

( x i ) SEQUENCE DESCRIPTION: SEQ ID NO:21:

```
Ala Asn Xaa Pro Xaa His Xaa Ala Pro Leu Gly Xaa Xaa Arg Pro Ser
1               5                   10                  15

Ala Pro Pro Leu Pro Xaa Val Xaa Asp Leu Pro Gln Xaa Gly Xaa Arg
            20                  25                  30

Arg
```

HEPATITIS E VIRUS PEPTIDES AND METHODS

This application is a continuation-in-part of U.S. application Ser. No. 07/876,941, filed May 1, 1992, and U.S. application Ser. No. 07/870,985, filed Apr. 20, 1992, which are both continuation-in-part applications of U.S. application Ser. No. 07/822,335, filed Jan. 17, 1992, now abandoned, which is a continuation-in-part of U.S. application Ser. No. 07/681,078, filed Apr. 5, 1991, now abandoned, which is a continuation-in-part application of U.S. application Ser. No. 07/505,888, filed Apr. 5, 1990, now abandoned, which is a continuation-in-part of U.S. application Ser. No. 420,921, filed Oct. 13, 1989, now abandoned, which is a continuation-in-part of U.S. application Ser. No. 367,486, filed Jun. 16, 1989, now abandoned, which is a continuation-in-part of U.S. application Ser. No. 336,672, filed Apr. 11, 1989, now abandoned, which is a continuation-in-part of U.S. application Ser. No. 208,997, filed Jun. 17, 1988, now abandoned, all of which are herein incorporated by reference.

1. FIELD OF INVENTION

This invention relates to peptide antigens of the enterically transmitted nonA/nonB hepatitis viral agent, also referred to herein as hepatitis E virus (HEV). The peptide antigens are useful in diagnostic methods and assays for ET-NANB hepatitis in humans.

2. REFERENCES

Arankalle, V. A., et al., The Lancet, 550 (Mar. 12, 1988).

Bradley, D. W. et al., Proc. Nat. Acad. Sci., USA, 84:6277 (1987).

Chauhan et al., Lancet, 341:149 (1993).

Chomczynski, P. et al., Anal. Biochem. 162:156 (1987).

Harlow, E. et al., *Antibodies: a Laboratory Manual*, Cold Spring Harbor Laboratory Press, Cold Spring Harbor, N.Y. (1988).

Huang, C—C et al., Virology, 1991:550 (1992).

Khuroo, M. S., *Am. J. Med.*, 48:818 (1980).

Lanford, R. E., et al., In Vitro Cellular and Devel Biol, 25 (2):174 (1989).

Maniatis, T., et al. *Molecular Cloning: A Laboratory Manual*, Cold Spring Harbor Laboratory (1982).

Sambrook, J. et al., *Molecular Cloning: A Laboratory Manual*, Cold Spring Harbor Laboratory. (1989).

Summers, M. D. et al., *A Manual of Methods for Baculovirus Vectors and Insect Cell Culture Procedures*, Texas Agricultural Experimental Station Bulletin No. 1555, 1988.

Tam, A., et al., Virology, 185:120 (1991-a).

Tam, A., et al., Hepatitis E virus: cDNA isolation and sequencing, p. 521–524. In Hollinger, F. B. et al. (ed.), Viral Hepatitis and Liver Disease. Williams and Wilkens, Baltimore. (1991-b).

Yarbough, P. O., J. Virology, 65(11):5790 (1991).

3. BACKGROUND OF THE INVENTION

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although there is some evidence of person to person transmission. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle, 1988). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. Occasionally the course of disease can be severe, however, as was recently shown by a human volunteer (Chauhan 1993). One peculiar epidemiologic feature of this disease, however, is the markedly high mortality observed in pregnant women; this is reported in numerous studies to be on the order of 10–20%. This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

4. SUMMARY OF THE INVENTION

It would therefore be useful, for diagnosing hepatitis E virus (HEV) infection, to provide HEV peptide antigens which are immunoreactive with sera from individuals known to be infected with HEV. Such antigens could be used in either a simple solid phase or homogeneous antibody-binding assay for rapid determination of antibodies which are diagnostic of HEV infection. It is one general object of the invention to provide HEV peptide antigens which are specific for serum from individuals infected with hepatitis E virus.

Another object of the invention is to provide a simple, rapid and relatively inexpensive immunoassay which uses such antigens.

Specific embodiments include an SG3 derived peptide, preferably, comprising a peptide antigen containing the epitope formed by the carboxyl terminal 327 amino acids of an HEV capsid protein. More preferably, the SG3 peptide antigen contains an amino acid sequence selected from the group consisting of SEQ ID NO:13, SEQ ID NO:14, homologous sequences therewith, and fragments, analogs, polymers and chimeras thereof. Even more preferably, the SG3 peptide contains the epitope formed by an amino acid sequence selected from the group consisting of SEQ ID NO:13, SEQ ID NO:14, and homologous sequences therewith.

The invention further includes a kit and method for detecting HEV infection in a test individual. In the detecting method, an antigen of the type described is reacted with serum from the test individual, and then examined for the presence of bound antibody. A second HEV peptide antigen may also be reacted with serum from the test individual, and then examined for the presence of bound antibody. The assay system includes a solid phase system, in which the antigen is carried on a solid support, or a homogeneous system, in which the antigen is associated with a reporter, where antibody binding to the antigen modulates the reporter signal when detected.

These and other objects and features of the invention will become more fully understood when the following detailed description of the invention is read in conjunction with the accompanying figures.

BRIEF DESCRIPTION OF THE DRAWINGS

FIGS. 2A, 2B, 2C and 2D, "Nucleotide Sequence of ORF-2 and ORF-3", the nucleotide sequences of the HEV ORF2 and ORF3 for Burma (upper line) and Mexico (lower line) strains of HEV;

FIG. 3, "Amino Acid Sequence of ORF-3", shows the amino acid sequences of the ORF3 protein for Burma (upper line) and Mexico (lower line) strains of HEV;

FIGS. 4A and 4B, "Amino Acid Sequence of ORF-2", show the amino acid sequences of the ORF2 protein for the Burma (upper line) and Mexico (lower line) strains of HEV;

DETAILED DESCRIPTION OF THE INVENTION

I. Definitions

Figure 1:
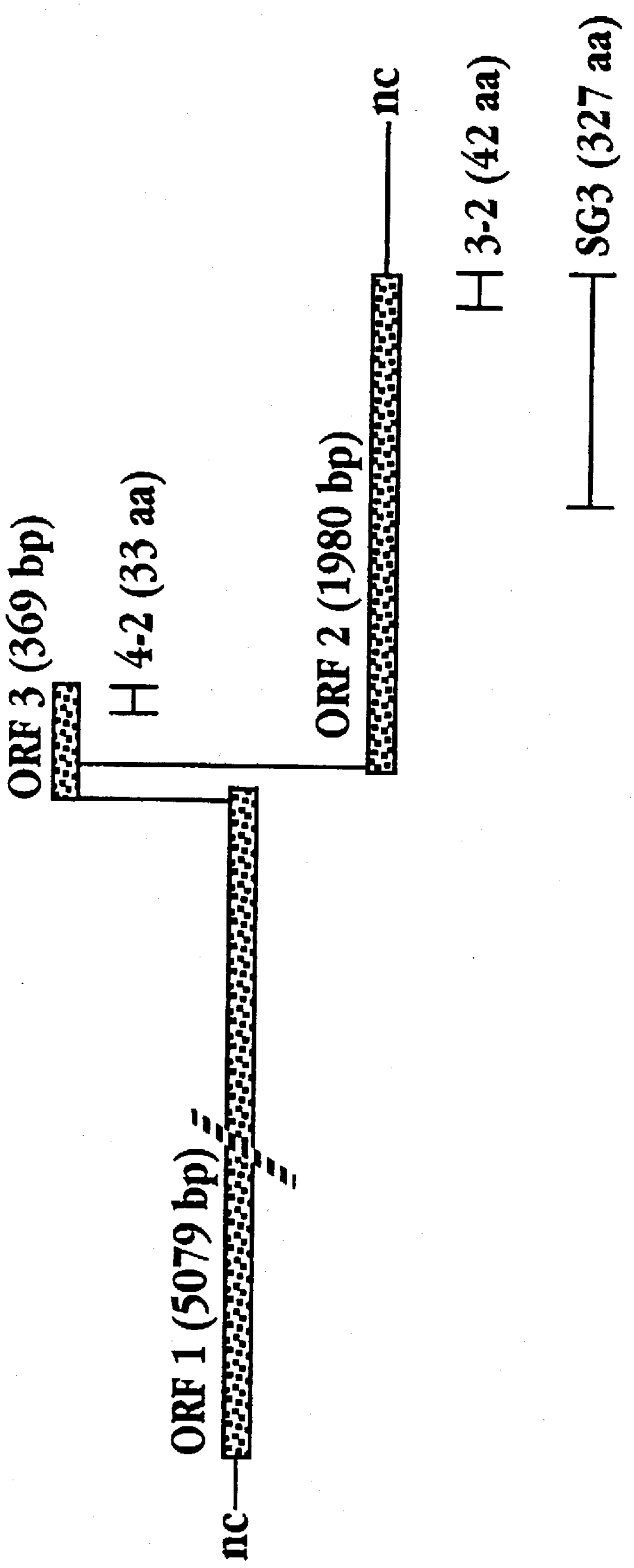
FIG. 1, "Genomic Organization of HEV", shows the HEV genome, the arrangement of open reading frames in the genome, and the approximate coding regions for peptides 406.3-2, 406.4-2, and SG3.

The terms defined below have the following meaning herein:

1. "Enterically transmitted non-A/non-B hepatitis viral agent", "hepatitis E virus", or "HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in *E. coli* strain BB4 identified by ATCC deposit number 67717.

2. Two nucleic acid fragments are "homologous" if they are capable of hybridizing to one another under hybridization conditions described by Maniatis et al., at pp. 320–323. However, using the following wash conditions: 2X SCC, 0.1% SDS, room temperature twice, 30 minutes each; then 2X SCC, 0.1% SDS, 50° C. once, 30 minutes; then 2X SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an HEV viral agent if it has the same or substantially the same basepair sequence as a region of the viral agent genome.

5. A protein or peptide is "derived from" an HEV viral agent if it is encoded by an open reading frame of a DNA or RNA fragment derived from an ET-NANB viral agent.

6. In two or more known peptide sequences which are more than about 70% homologous in amino acid sequence, a third amino acid sequence will be "internally consistent with the known sequences" if each amino acid in the third sequence is identical to at least one of the amino acids in the known sequences.

7. The term "antigen" refers to a molecule which is specifically recognized and bound by antibodies contained in human sera. The terms "immunogenic region" or "epitope" are used interchangeably herein to indicate that region of an antigen which is specifically recognized by an antibody in human sera.

8. The "epitope formed by" a given amino acid sequence is the epitope produced by the secondary/tertiary structure of that sequence in aqueous solution.

9. The "antigen binding site" is that region of an antibody molecule contained within the variable regions of the antibody which directly participates in binding the antigen.

10. A specified "peptide antigen containing the epitope formed by" a specified amino acid sequence includes the specified sequence itself or a portion thereof which is sufficient to define the epitope present in the specified sequence, as evidenced by immunoreactivity to an antibody contained in a human sera sample. The specified peptide antigen may include amino acid substitutions which preserve the epitope.

II. HEV Peptide Antigens

This section describes methods for preparing HEV peptide antigens useful as diagnostic reagents in accordance with the invention.

A. HEV Genomic Sequences

HEV genomic clones, and sequences corresponding to the entire HEV genome for different HEV strains were obtained according to published methods (Huang 1992, Yarbough 1991) and as described in the parent applications referenced above. Briefly, RNA isolated from the bile of a cynomolgus monkey having a known HEV infection was cloned, as cDNA fragments, to form a fragment library, and the library was screened by differential hybridization to radiolabeled cDNAs from infected and non-infected bile sources.

The basepair sequence of cloned regions of the HEV fragments in identified clones was determined by standard sequencing methods. With reference to FIG. 1, HEV is a virus with an approximately 7.5 kilo base (kb) single-stranded and polyadenylated RNA genome of positive-sense polarity. Three open reading frames (ORFs) have been assigned to HEV as ORF1, encoding polypeptides with domains of the RNA-directed RNA polymerase and a helicase, ORF2, encoding the putative capsid protein of the virus, and ORF3, a second putative structural protein.

The genomic organization of HEV assigns its non-structural gene(s) at the 5' terminus with the structural gene(s) at the 3' end. Two subgenomic polyadenlated transcripts of approximately 2.0 kb and 3.7 kb in sizes are detected in infected liver and co-terminated at their 3' ends with the 7.5 kb full-length genomic transcript. The genomic organization and expression strategy of HEV suggest that it might be the prototype human pathogen for a new class of RNA virus or perhaps a separate genus within the Caliciviridae family.

The genomic and peptide sequences shown in FIGS. 2A, 2B, 2C and 2D correspond to the ORF-2 and ORF-3 regions of Burma (B) (upper lines) and Mexico (M) strains (lower lines) of HEV. The bases indicated in the middle lines represent conserved nucleotides. The numbering system used in the comparison is based on the Burma sequence. The region corresponding to ORF2 has SEQ ID Nos. 1 and 2 for the Burma and Mexico strains, respectively. The region corresponding to ORF3 has SEQ ID Nos. 3 and 4 for the Burma and Mexico strains, respectively. The region corresponding to 406.3-2 has SEQ ID Nos. 5 and 6 for the Burma and Mexico strains, respectively. The region corresponding to SG3 has SEQ ID Nos. 7 and 8 for the Burma and Mexican strains, respectively. The region corresponding to 406.402 has SEQ ID Nos. 9 and 10 for the Burma and Mexico strains, respectively. B. HEV Peptide Sequences The amino acid sequences corresponding to the third and second open reading frames of the Burma and Mexico strains of HEV are given in FIGS. 3 and 4, respectively. The sequence listings shown are as follows:

SEQ ID Nos. 11 and 12 correspond to the amino acid sequences for the peptides 406.3-2 (B) and 406.3-2 (M), respectively. Each peptide is a 42 amino acid peptide in the C-terminal end region of capsid protein encoded by the ORF2, as indicated in the ORF2 sequence (FIGS. 4A and 4B).

SEQ ID Nos. 13 and 14 correspond to the amino acid sequences for the peptides SG3 (B) and SG3 (M), respectively. Each peptide includes the carboxyl 327 amino acids of the HEV capsid.

SEQ ID Nos. 15 and 16 correspond to the amino acid sequences for the entire putative capsid protein encoded by the Burma and Mexico strain ORF2, respectively.

SEQ ID Nos. 17 and 18 correspond to the amino acid sequences for the 406.4-2 (B) and 406.4-2 (M), respectively (FIG. 3). These are 33 amino acid sequences encoded by the ORF3.

SEQ ID Nos. 19 and 20 correspond to the amino acid sequences for the entire protein encoded by ORF3 of the Burma and Mexico strains, respectively.

Also contemplated are sequences which are internally consistent with the above specified sequences from different strains of HEV antigens. These include Sequence ID No. 11; Sequence ID No. 12, and internally consistent variations between Sequence ID Nos. 11 and 12; Sequence ID No. 13; Sequence ID No. 14, and internally consistent variations between Sequence ID Nos. 13 and 14; Sequence ID No. 15; Sequence ID No. 16; and internally consistent variations between Sequence ID Nos. 15 and 16; Sequence ID No. 17; Sequence ID No. 18; and internally consistent variations between Sequence ID Nos. 17 and 18; Sequence ID No. 19; Sequence ID No. 20, and internally consistent variations between Sequence ID Nos. 19 and 20.

For example, the HEV 406.4-2 antigens have the sequence homology shown below for the Burma (B) and Mexico (M) strains. The single dots in the sequence comparison indicate recognized high-probability or "neutral" amino acid substitutions. The blank spaces indicate a non-neutral substitution.

```
                              10        20        30
MEXICAN(SEQ ID NO.18)  ANQPGHLAPLGEI RPSAPPLPPVADLPQPGLRR
                       ::.:.: :::: .::::::::.:.:::: : ::
BURMA(SEQ ID NO.17)    ANP PDHSAPLGVTRPSAPPLPHVVDLPQLGPRR
                              10        20        30
```

A sequence which is internally consistent with these two sequences would have one of the sequences:

AN(Q/P)P(G/D)H(L/S)APLG(E/V) (I/T)RPSAPPLP(P/H)V(A/V)DLPQ (P/L)G(L/P)RR, (SEQ ID NO:21) where X/Y means either amino acid X or amino acid Y.

The ORF3 amino acid sequences, 124 amino acids in length, for the Burma and Mexico strains have an 87.1% identity in the 124 amino acids. The ORF2 amino acid sequences, having 659 amino acids of overlap, have a 93.0% identity in the 659 amino acids.

C. Preparation of HEV Peptides

To prepare the 406.3-2 (M) peptide, DNA fragments from the lambda gt11 406.3-2 described in Example 1 was subcloned into the glutathione S-transferase vector pGEX™ to express the 406.3-2(M) antigen, as detailed in Example 1, and in the Tam (1991-b) reference.

The 406.3-2(B) antigen can be prepared by PCR amplification of the Burma SEQ ID No. 5 from above by PCR amplification of the pBET1 plasmid (Tam 1991-b). This plasmid contains a 2.3 kb insert covering the ORF2 and ORF3 for Burma strain HEV sequence. The plasmid is amplified by PCR amplification, using a 5' primer containing an NcoI site and a 3' primer containing a BamHI site (Sakai). The amplified fragment is inserted into the NcoI/BamHI site of a pGEX™ vector, and expressed in an *E. coli* expression system as described in Example 1.

The SG3(B) peptide was prepared by first amplifying the SEQ ID No. 7 sequence with 5' EcoRI-NcoI and 3' BamHI linkers, using a pBET1 clone plasmid containing the entire ORF2 and ORF3 regions of HEV (B). The amplified fragment was inserted into the EcoRI/BamHI site of a Bluescript™ vector (Stratagene, La Jolla, Calif.), according to the manufacturer's instructions. After vector propagation and harvesting, the cloned insert was released by digestion with NcoI and BamHI, and gel purified. The purified fragment was inserted into the NcoI/BamHI site of a pGEX™ vector, and expressed in an *E. coli* expression system as described in Example 1. The SG3(M) peptide can be prepared similarly, using the SEQ ID No. 8 in place of the SEQ ID No. 7.

The capsid protein (B) was prepared substantially as described above by PCR amplification of the SEQ ID No. 1, from a pBET1 plasmid using a 5' primer containing an NcoI site and a 3' primer containing a BamHI site. The amplified fragment was inserted into the NcoI/BamHI site of a pGEX™ vector, and expressed in an *E. coli* expression system as described in Example 1. The capsid protein (M) is similarly prepared.

To prepare the 406.4-2(M) peptide, the lambda gt11 406.4-2 described in Example 1 was subcloned into the glutathione S-transferase vector pGEX™ to express the 406.4-2(M) antigen, as detailed in Example 1.

The 406.4-2(B) antigen can be prepared by PCR amplification of the Burma SEQ ID No. 9 from above by PCR amplification, using a 5' primer containing an NcoI site and a 3' primer containing a BamHI site. The amplified fragment is inserted into the NcoI/BamHI site of a pGEX™ vector, and expressed in an *E. coli* expression system as described in Example 1.

It will be appreciated that other HEV peptides, e.g., fragments, polymers, analogs, and chimeric peptides, containing selected portions, and preferably C-terminal portions, of the HEV capsid protein (ORF-2) containing the SG3 sequence and ORF-3 proteins containing the 406.4-2 sequence, can similarly be prepared, using the HEV genomic-insert plasmids above, with amplification of the desired sequences and cloning into a suitable expression vector, as outlined above, and detailed in Example 1.

Peptide fragments, analogs, chimeras, and polymers produced in this manner may be screened for antigenicity by the method described in Example 4. Briefly, the peptides are purified by techniques known to those skilled in the art, for example, by the method of Example 3, and plated onto wells of microtitre dishes. The peptides are washed with blocking solution and then reacted with sera known to contain anti-HEV antibodies. The unbound antibodies are washed away and a second antibody conjugated to a reporter molecule is then reacted with the peptide-antibody complexes. Results may be obtained, after washing away unbound second antibody, by detection of the reporter molecule.

The HEV peptide fragments, polymers, chimeras, and analogs produced in this manner consist of the essential epitopic region(s) of an SG3 peptide in accordance with the invention, are those that show substantially similar immunoreactivity to HEV positive sera as does an SG3 peptide antigen (SEQ ID No. 13 or 14). Immunoreactivity is substantial similar when the percentage of sera samples that are reactive with both SG3 and the peptide fragment, analog, chimera, or polymer is, preferably, greater than 80%, more preferably greater than 90%, and even more preferably greater than 95%.

It will also be appreciated that HEV peptides may similarly be produced in other types of cells; e.g., yeast, insect, and mammalian, when transfected with an appropriate expression vector containing HEV peptide sequences. Such modifications can be easily made by those of ordinary skill in the art. General methods, for example, for handling and preparing baculovirus vectors and baculoviral DNA, as well as insect cell culture procedures, are outlined in *A Manual of Methods for Baculovirus Vectors and Insect Cell Culture Procedures* (Summers, M. D. et al., 1988).

The coding sequences used in producing the recombinant peptides can be derived from the cloning vectors described above and detailed elsewhere (Tam 1991-a), or from synthetic nucleotide synthesis using PCR splicing methods to join oligonucleotide fragments, according to known methods, in building up nucleotide sequences.

D. Mature Capsid Protein

HEV peptide antigens may also be obtained from purified HEV virus propagated in primary hepatocytes obtained from primate liver, preferably from human or cynomolgus monkey liver. Methods for preparing primary primate hepatocytes for culture, and culture medium conditions effective to preserve liver-specific functions for extended periods in culture are detailed for human hepatocytes in Example 2 below.

After 3 days of growth in culture, the cells are infected with a pooled inoculum of HEV-infected cynomolgus monkey stool pool (fourth passage), as detailed in Example 3. The presence and level of propagating HEV virus in the cells can be measured by indirect immunofluorescence. Where, for example, the primary cells are cynomolgus cells, the cells can be immunoreacted with human HEV anti-sera, followed by immunoreaction with rabbit anti-human IgG antibodies.

Alternatively, the HEV virus can be detected and measured by selective amplification methods involving initial cDNA formation, and PCR amplification of HEV cDNA sequences by PCR amplification, as detailed in Example 3.

Virus particles can be isolated from HEV infected human hepatocytes in culture medium by pelleting the virus through a 30% sucrose cushion by ultracentrifugation. The pelleted virus may be further purified, if desired, by zonal centrifugation through a 10–40% sucrose gradient, combining peak virus fractions.

Other methods for separating virus particles from soluble culture-medium components may be used. For example, clarified culture medium can be passed through a size-exclusion matrix, to separate soluble components by size exclusion.

Alternatively, the clarified culture medium can be passed through an ultrafiltration membrane having a 10–20 nm pore size capable of retaining virus particles, but passing solute (non-particulate) culture medium components.

The present invention allows for glycosylation and other post-translation modifications in intact HEV capsid protein. Capsid isolation from the viral particles can be carried out by standard methods, such as ion exchange and size-exclusion chromatography, and HPLC purification, after solubilization of the virus particles in a solubilizing medium, such as a solution of a non-ionic surfactant. The protein may be purified by affinity chromatography, employing, for example, antibodies purified from anti-HEV antisera. Degradative processes may be employed to obtain partial fragments and peptides from the intact capsid protein (as well as recombinantly produced proteins); e.g. proteases may be employed. Such procedures are known to those skilled in the art.

E. Synthetic Production of HEV Peptides

In addition to the procedures for producing the peptides described above, peptides of up to about fifty amino acids in length may be produced by conventional solid phase synthesis methods. Such methods are known to those skilled in the art. Peptides produced in this manner may be covalently linked to other peptides or protein conjugates or moieties, as would be formed, for example, recombinantly in a fusion protein.

III. Peptide Antigen Diagnostic Method

In a related aspect, the invention is directed to a method of diagnosing individuals with HEV infections wherein HEV derived peptide antigens are used to examine an individual's serum for the presence of anti-HEV antibodies.

A. Immunoreactivity of Peptide Antigens

Following production of peptide antigens, in accordance with the invention, serum samples from individuals known to be infected with HEV are tested for their ability to bind to such antigens. Assays for antibody-antigen binding are well known in the art (Harlow, 1988). Solid-phase assays, such as enzyme-linked immunosorbent assay (ELISA) binding assays are particularly suitable for measuring antibody-peptide antigen binding. Such assays may be carried out in direct or competitive binding assay format. In the direct method, the test peptide is adsorbed to a solid phase. Test anti-HEV antisera is added to the peptide, and binding of human antibody to the peptide is measured, for example, as in the method of Example 4.

Alternatively, when peptides are expressed as fusion proteins of sufficient size to be retained by an SDS-PAGE, western blots may be used to determine binding of the peptide portion of the fusion protein to a serum sample.

Clones 406.3-2(M) and 406.4-2(M) were shown to encode immunoreactive peptides in co-owned U.S. patent application, Ser. No. 07/505,888, already incorporated herein by reference. In continuing studies with these peptides and their analogs from the Burma strain, with HEV-positive human sera (from five different epidemics), peptide 406.3-2(M) was immunoreactive with eight of eleven samples tested, peptide 406.4-2(M) was immunoreactive with nine of eleven samples tested, and peptides 406.3-2(B) and 406.4-2 were both immunoreactive with all six of six samples tested (Yarbough 1991). A description of experiments leading to the above results may be found in Example 1.

In the present invention, bacterially expressed HEV peptides including 406.3-2(M) and 406.4-2(M) discussed above, and also including 406.4-2(B) and SG3(B), were extensively tested separately and in combinations for immunoreactive sensitivity to a number of different human antisera obtained from individuals with hepatitis from sources around the world. The enzyme-linked immunosorbent assay (ELISA), was used to test the immunoreactivity of the peptides as described in Example 4.

The following combinations of peptides were used to co-coat microtitre wells prior to testing;

a) 406.4-2(M) and 406.4-2(B), b) 406.4-2(M), 406.4-2(B) and 406.3-2(M), and c) SG3(B) alone.

Sera used in immunoreactive testing was collected from both sporadic cases, as well as outbreaks, of hepatitis. The sera used is described in Example 4.

Addition of the immunoreactivity data of peptide SG3(B) (SEQ ID NO:13) to the data for the combination of ORF-2 and ORF-3 immunoreactive peptides (406.4-2(M), 406.3-2 (M), and 406.4-2(B)) increased the overall HEV cases detected, as can be seen from Table 1, following. Detection of both anti-HEV IgG and IgM antibodies increased with the addition of SG3. The combination of peptides including the SG3 data "the peptide combination" detected IgG and IgM antibodies in 170 of the samples tested: 42 sera samples in a Korean sera panel contained IgG reactive with the peptide combination; 73 sera samples tested in a Pakistani/Belize sera panel contained IgG reactive with the peptides and 20 serum samples from the same panel contained IgM reactive with the peptide combination; finally, 55 serum samples in a Saudi sera panel contained IgG reactive with the peptide combination and 35 of 35 serum samples from the same panel contained IgM reactive with the peptide combination.

The combined improvement (calculated for all the panels) in IgG detection achieved by the addition of the SG3 data to the data for the combination of smaller immunoreactive peptides was 29%; i.e., 49 additional serum samples, for a total of 170, were detected which contain HEV positive antibodies with the combination of peptides including SG3. The improvement in IgM detection was 53%.

TABLE 1

Reactivity of Bacterially Expressed Recombinant HEV Peptides

| Sera Source (Peptide Regions) | Number of Antigens | Number of Samples (% Total Positives) IgG | IgM |
|---|---|---|---|
| Korean Panel, Kim et al | | | |
| (ORF3)[2] | 2 | 29 (69%) | NT |
| (ORF2/3)[3] | 3 | 30 (71%) | NT |
| (ORF2/3) (Including SG3)[4] | 4 | 42 (100%) | NT |
| SG3 unique | 1 | 12 (29%) | NT |
| Pakistani/Belize Panel (Ticehurst et al) | | | |
| (ORF3)[2] | 2 | 29 (40%) | 0 (0%) |
| (ORF2/3)[3] | 3 | 43 (59%) | 2 (10%) |
| (ORF2/3) (Including SG3)[4] | 4 | 73 (100%) | 20 (100%) |
| SG3 unique | 1 | 30 (41%) | 18 (90%) |
| Saudi Panel (Purcell et al) | | | |
| (ORF3)[2] | 2 | 40 (73%) | 3 (90%) |
| (ORF2/3)[3] | 3 | 47 (87%) | 24 (69%) |
| (ORF2/3) (Including SG3)[4] | 4 | 55 (100%) | 35 (100%) |
| SG3 unique | 1 | 7 (13%) | 11 (31%) |

Footnote:
[2]ORF3 antigens include 406.4-2(B) and 406.4-2(M).
[3]ORF2/3 antigens are 406.4-2(B) and (M), and 406.3-2(B).
[4]ORF2/3 antigens are 406.4-2(B) and (M), 406.3-2, and SG3.

It is apparent that there are both IgG and IgM antibodies contained in some of the serum samples which recognize one or more epitopes unique to SG3. Many of these samples can only be detected by reactivity to SG3; i.e., these samples do not contain antibodies to the smaller peptides. Forty-one percent (41%) of the Pakistani/Belize panel, for example, contained IgG which was reactive with the combination of peptides only after the addition of SG3. Similarly, ninety percent (90%) of the reactive sera in the Pakistani/Belize panel contained IgM reactive with the combination only after addition of SG3. These results indicate important SG3 epitope(s) which are unique to this peptide. Of additional importance, the unique epitope(s) appear to be dominant; i.e., broadly reactive with sera from many HEV outbreaks around the world.

Peptide SG3 was further tested for its immunoreactivity to IgM and IgG serum components in serum samples taken from individuals at the following stages of HEV infection; acute, early convalescent, and convalescent, as detailed in Example 5. The ELISA techniques described in Example 4 were again used, however, sera was tested for reactivity to the peptides 406.3-2(M), 406.4-2(B), 406.4-2(M), and SG3 each coated in separate wells of microtitre plates. Sera was collected from individuals in the Pakistani outbreak described in Example 4, during acute, early convalescent, and convalescent stages of infection; collections occurred in August, September and December respectively (Ticehurst). Non-A, non-B hepatitis infection in the individuals from whom samples were taken was confirmed by serological testing with commercially available tests and by either reverse transcriptase-polymerase chain reaction (RT-PCR) or by bona fide clinical symptoms as described in Example 5. The results of the immunoscreening are presented in Table 2, following.

TABLE 2

SG3 Antigen for Detecting Anti-HEV (Abbottabad, Pakistan Outbreak)

| Stage | No. Assayed | SG3(B) | 406.3-2(M) | 406.4-2(B) | 406.4-2(M) |
|---|---|---|---|---|---|
| | | Anti-HEV IgM | | | |
| Acute | 26 | 11 (42%) | 2 (8%) | 0 | 0 |
| Early conv. | 18 | 8 (44%) | 0 | 0 | 0 |
| Conv. | 19 | 0 | 0 | 0 | 0 |
| | | Anti-HEV IgG | | | |
| Acute | 26 | 24 (92%) | 17 (65%) | 13 (50%) | 7 (27%) |
| Early Con. | 17 | 16 (94%) | 10 (59%) | 12 (71%) | 4 (24%) |
| Conval. | 18 | 126 (89%) | 4 (22%) | 1 (6%) | 0 |

The SG3 peptide antigen was able to detect a significantly higher proportion of both IgM and IgG antibodies during all three stages of infection than any of the shorter peptides. Peptide SG3 was able to detect IgG in 89% of the HEV positive convalescent sera tested whereas IgG was detected in only 22% of the same convalescent sera by the best of the three shorter peptides, 406.3-2(M). Peptide SG3 was better than any of the shorter peptides at detecting IgG in acute and early convalescent sera as well. Peptide SG3 may contain an immunodominant epitope resulting in its improved immunoreactivity. Antibodies which are specifically reactive with this epitope may remain in the serum longer than the shorter peptides resulting in the higher (89%) IgG reactivity to SG3 as compared to 22% for 406.3-2(M) in the convalescent stage sera.

SG3 shows a marked increase in detection of IgM over all of the other peptides. Detection of IgM was up to 44% with SG3 while only 8% with the other peptides. IgM antibodies, while detected by peptide SG3 in acute and early convalescent sera, were not detected at all in convalescent sera indicating the normal reduction in IgM levels with the progression of disease.

The results obtained above illustrate the usefulness of the SG3 peptide as a diagnostic reagent. Peptide SG3 has high sensitivity for antibodies found in sera from individuals afflicted with non-A, non-B hepatitis during all three stages of infection.

B. Reactivity of Anti-HAV, -HBV, and -HCV antisera to Peptide SG3

In accordance with the invention, the peptide antigens useful in methods for diagnosing HEV infection are specific for antibodies reactive to HEV; i.e., the HEV peptide antigens are not cross-reactive with sera from uninfected individuals and particularly with sera from those individuals not infected with HEV but who are infected with other hepatitis viral agents. Such other hepatitis agents include hepatitis A virus (HAV), hepatitis B virus (HBV), and hepatitis C virus (HCV).

The peptide antigens useful in diagnostic methods and kits may be tested for specificity by examining the reactivity of the peptides with sera specific for HAV, HBV, and/or HCV. One may obtain sera specific for hepatitis agents by taking samples from individuals with confirmed infections.

Alternatively, one may elicit an immune response in an animal by injecting the animal with viral peptides through techniques well known in the art, and subsequently testing sera samples taken from the animal for reactivity to the HEV peptides, (see; e.g., Harlow et al., *Antibodies: A laboratory Manual*, 1988, Cold Spring Harbor Lab).

In the present invention, serum samples used for testing the HEV recombinant peptides, were taken from individuals in the United States and from individuals in the Middle East. All of the individuals who contributed serum samples had confirmed HAV, HBV or HCV infections. The serum samples were tested for reactivity to a combination of peptides 406.4-2(M), 406.4-2(B), 406.3-2(M) and SG3 in an ELISA format as described in Example 6. The results of this study are outlined in Table 3, following.

TABLE 3

Specificity of HEV Peptides for Anti-HEV IgM and IgG Antibodies

| Antisera | Number Tested | Antibodies to HEV IgG | IgM |
|---|---|---|---|
| Hepatitis A | | | |
| Middle East | 23 | 1 | 0 |
| U.S. | 6 | 0 | 0 |
| Hepatitis B | | | |
| Middle East | 100 | 29 | 2 |
| U.S. | 10 | 0 | 0 |
| Hepatitis C | | | |
| Middle East | 33 | 13 | 0 |
| U.S. | 15 | 0 | 0 |

No IgM or IgG in sera taken from the individuals in the United States was reactive with the combination of HEV peptides, including six HAV infected, ten HBV infected, and fifteen HCV infected samples, as can be seen from Table 3. IgG was detected, however, in several of the samples taken from individuals in the Middle East, including; 1/29 HAV, 29/100 HBV, and 13/33 HCV infected individuals. In contrast, anti-HEV IgM was detected in only 2 of the 162 middle eastern sera samples. These results most likely indicate that only 2 of these individuals had acute HEV infections (probably co-infections with another hepatitis virus). The high level of reactive IgG, on the other hand, is indicative of a high rate of exposure to HEV in this part of the world.

These results demonstrate that the combination of HEV peptides is not cross-reactive with sera taken from individuals infected with other viral hepatitis agents. SG3 and the combination of HEV derived peptides, therefore, is not only highly sensitive as demonstrated above, it is also specifically reactive with antibodies found in serum from humans infected with the hepatitis E virus.

IV. Peptide Antigens for ET-non-A/non-B Viral Hepatitis Assays

This section describes the peptide antigens which are employed in the assay kit and assay method described in Section V below.

A. HEV Specific Peptide Antigens

In accordance with the invention, peptide antigens, characterized as useful for diagnosis of HEV herein, include an SG3(B) or (M) peptide antigen having the epitope formed by an amino acid sequence selected from the group consisting of SEQ ID NO:13 and SEQ ID NO:14, or a homologous sequence thereof as long as the immunoreactivity of SG3 is preserved. Also contemplated are analogs, polymers, fragments, and chimeric peptides derived from the amino acid sequence of an SG3 peptide antigen, so long as the immunoreactivity of these peptides is substantially similar to the immunoreactivity of SG3 (SEQ ID NO: 13 and SEQ ID NO:14).

Antigenic peptide SG3 is derived from the carboxyl-terminal 327 residues of the capsid protein which is encoded by open reading frame-2. Peptide SG3 was first described in co-owned U.S. patent application, "Hepatitis E Virus Vaccine and Method, Ser. No. 07/870,985, filed Apr. 20, 1992, already incorporated by reference, for use in a vaccine composition. This peptide, however, has not been characterized for use in a diagnostic method prior to the present application. The sequences of SG3(B) and (M) can be found in FIGS. 2 and 4. These peptide antigens can be prepared as described in Section II above and in Example 1 which follows.

Studies conducted in support of the present invention, discussed above, demonstrate that the SG3(B) peptide antigen is specific for HEV; i.e., SG3(B) immunoreacts with antibodies present in the serum of HEV infected individuals. The antigen may not detect all HEV positive sera, and may pick up some false positives; i.e., non-infected individuals. The SG3(M) peptide can likewise be expected to specifically immunoreact with antibodies present in HEV infected individuals.

Several peptide antigens have been previously characterized in co-owned U.S. patent application for "Enterically Transmitted Non-A/Non-B Hepatitis Viral Agent and Characteristic Epitopes Thereof," Ser. No. 07/420,921, filed Apr. 5, 1990, already incorporated by reference, now abandoned. These peptides form part of the present invention when used in assays in combination with the SG3 derived peptides.

A first antigen in the group of previously characterized HEV peptide antigens contains the epitope formed by the 406.4-2(B) peptide (SEQ ID NO:17), or the 406.4-2(M) peptide (SEQ ID NO:18). Also contemplated are peptide antigens containing the epitope formed by an amino acid sequence homologous with or an internally consistent variation between SEQ ID Nos: 17 and 18. This first peptide antigen is derived from the carboxyl terminus of the protein encoded by open reading frame-3. A second peptide antigen contains the epitope formed by the 406.3-2(B) peptide (SEQ ID NO:11) or the 406.3-2(M) peptide (SEQ ID NO:12). Also contemplated as a second peptide antigen are peptide antigens containing the epitope formed by an amino acid sequence homologous with or an internally consistent variation between SEQ ID Nos: 11 and 12. This second peptide is derived from the carboxyl terminus of the capsid protein encoded by open reading frame-2. FIG. 3 shows the sequence of the 406.4-2(B) and (M) peptides and FIGS. 4A and 4B shows the sequence of the 406.3-2(B) and (M) peptides. Methods for obtaining the confirmatory peptides are described above and detailed in the following Examples.

Studies conducted in support of the present invention, also discussed in Example 1 following, demonstrate that the above known HEV peptide antigens detect infection with hepatitis E virus; i.e., the antigens immunoreact with antibodies present in humans infected with HEV. The antigens may not detect all HEV positive individuals, and may pick up some false positives; i.e., non-infected individuals.

In accordance with the present invention, reactivity of antibodies in a serum sample taken from an individual suspected of being infected with a causative agent of hepatitis to peptide SG3 is a reliable method for diagnosing the causative agent as HEV. Also forming part of the present invention, reactivity to the known peptides used in conjunction with SG3 may enhance the sensitivity and reliability of the diagnostic method described below.

V. Utility

This section describes uses of the antigenic peptides of the invention as diagnostic reagents for diagnosing hepatitis E viral infection.

A. Diagnostic Methods and Kits

Three basic types of diagnostic applications of the peptide antigens will be described. The first is based on inhibition of complement-mediated, antibody-dependent cytolysis by the peptide. In this method, serum from a test individual is reacted with HEV-infected cultured human hepatocytes in the presence of complement. The presence of anti-HEV antibody is evidenced by cell lysis, as judged, for example, by trypan blue dye exclusion. Where cell lysis is observed, the specificity of the anti-HEV antibody for the HEV peptide antigen is demonstrated by first reacting the serum with excess peptide antigen, then mixing the serum with the cells in the presence of complement. Antibody specificity is indicated by a substantial decrease in cell lysis. The method can also be used to quantitate the antibody titre in the analyte serum, by titrating the serum with increasing amounts of peptide concentration where a noticeable effect on the extent of cell lysis is first observed.

The second general assay type is a solid-phase immunoassay. In this method, a solid phase reagent having surface-bound peptide is reacted with analyte serum, under conditions which allow antibody binding to the peptide on the reagent. After washing the reagent to remove unbound serum components, the reagent is reacted with reporter-labeled anti-human antibody to bind reporter to the reagent in proportion to the amount of bound anti-HEV antibody on the solid support. The reagent is again washed to remove unbound labeled antibody, and the amount of reporter associated with the reagent is determined. Typically, as in the system described in Example 1, the reporter is an enzyme which is detected by incubating the solid reagent in the presence of a suitable fluorometric or colorimetric substrate. However, radiolabel and other reporters may be used.

After reacting the analyte serum with the solid-phase bound antigen and washing to remove the unbound serum components, one may alternatively use the peptide antigen itself bound to reporter as a detection reagent instead of using an anti-human antibody as a reporter mediator. The competitive assay takes advantage of antibody bivalency. The same reporters may be used in this embodiment of the solid-phase assay as was described above.

Multiple peptides may be used in conjunction or in tandem in each of the assays described above. In addition, reaction to each peptide may be distinguished. For example, in the solid-phase assay described above, two or more different peptides may be bound to solid phase in separate locations so that reaction to each peptide may be quantitated separately. Alternatively, peptide antigens labeled with distinguishable reporters may be used to detect peptides which are interspersed on the solid support.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group to a chemically reactive group on the solid support, such as an activated carboxyl, hydroxyl, or aldehyde group.

The third general assay type is a homogeneous assay, in which antibody binding to a solid support produces some change in the reaction medium. Known general types of homogeneous assays proposed heretofore include: (a) spin-labeled reporters, where antibody binding to the antigen is detected by a change in reporter mobility (broadening of the spin splitting peaks); (b) fluorescent reporters, where binding is detected by a change in fluorescence efficiency; (c) enzyme reporters, where antibody binding effects enzyme/ substrate interactions such as the system described in Example 4; and (d) liposome-bound reporters, where binding leads to liposome lysis and release of encapsulated reporter. The adaption of these methods to the peptides of the present invention follows conventional methods for preparation of homogeneous assay reagents.

In each of the three general assays described above, the assay method involves reacting the serum from a test individual with the antigen, and examining the antigen for the presence of bound antibody. In the first assay, the examining is done by observing the decrease in antibody-mediated cytolysis, when the antibody is bound to the peptide. In the solid-phase assay, the examining involves attaching a labeled anti-human antibody (or labeled peptide antigen) to the antibody being examined, and measuring the amount of reporter bound to the solid support. And in the third assay type, the examining is done by observing the effect of antibody binding on a homogeneous assay reagent.

The following examples, which illustrate various methods and compositions in the invention, are intended to illustrate, but not limit the scope of the invention.

Materials

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Mass.); and RNase A was obtained from Sigma (St. Louis, Mo.)

Other reagents: EcoRI linkers were obtained from NEB; and nitro blue tetrazolium (NBT), 5-bromo-4-chloro-3-indolyl phosphate (BCIP), 5-bromo-4-chloro-3-indolyl-B-D-galactopyranoside (Xgal), p-Nitrophenyl phosphate, and isopropyl B-D-thiogalactopyranoside (IPTG) were obtained from Sigma. cDNA synthesis kit and random priming labeling kits are available from Boehringer-Mannheim Biochemical (BMB, Indianapolis, Ind.).

Cloning and Expression vectors such as pBluescript™ (pBS), can be obtained from Stratagene Cloning Systems (La Jolla, Calif.) and the pGEX™ expression vector can be obtained from Pharmacia (Piscataway, N.J.).

Immunodiagnostic Test Kits for Hepatitis A Virus (HAV), Hepatitis B Virus (HBV), and Hepatitis C Virus (HCV), are available from Abbott Diagnostics (Abbott Park, Ill., USA).

EXAMPLE 1

Preparation of 406.3-2, 406.4-2, and SG3 Antigens

A. Production of Random HEV DNA Fragments

A pBET1 plasmid is digested with EcoRI to release the insert which is purified from the linearized plasmid by gel electrophoresis. The purified fragment is suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions are determined from a prior calibration study, in which the incubation time required to produce predominantly 100–300 basepair fragments is determined. The material is extracted with phenol/chloroform before ethanol precipitation.

The fragments in the digest mixture are blunt-ended and ligated with EcoRI linkers. The resultant fragments are analyzed by electrophoresis (5–10V/cm) on 1.2% agarose gel, using PhiX174/HaeIII and lambda/HindIII size markers. The 100–300 bp fraction is eluted onto NA45 strips (Schleicher and Schuell), which are then placed into 1.5 ml microtubes with eluting solution (1M NaCl, 50 mM arginine, pH 9.0), and incubated at 67° C. for 30–60 minutes. The eluted DNA is phenol/chloroform extracted and then precipitated with two volumes of ethanol. The pellet is resuspended in 20 ml TE (0.01M Tris HCl, pH 7.5, 0.001M EDTA).

B. Cloning in an Expression Vector

Lambda gt11 phage vector (Huynh) is obtained from Promega Biotec (Madison, Wis.). This cloning vector has a unique EcoRI cloning site 53 base pairs upstream from the beta-galactosidase translation termination codon. The genomic fragments from above, provided either directly from coding sequences or after amplification of cDNA, are introduced into the EcoRI site by mixing 0.5–1.0 ug EcoRI-cleaved gt11, 0.3–3 ul of the above sized fragments, 0.5 ul 10X ligation buffer (above), 0.5 ul ligase (200 units), and distilled water to 5 ul. The mixture is incubated overnight at 14° C., followed by in vitro packaging, according to standard methods (Maniatis, 1982, pp. 256–268).

The packaged phage are used to infect *E. coli* strain KM392, obtained from Dr. Kevin Moore, DNAX (Palo Alto, Calif.). Alternatively, *E. Coli* strain Y1090, available from the American Type Culture Collection (ATCC #37197), can be used. The infected bacteria are plated and the resultant colonies are checked for loss of beta-galactosidase activity-(clear plaques) in the presence of X-gal using a standard X-gal substrate plaque assay method (Maniatis). About 50% of the phage plaques will show loss of beta-galactosidase enzyme activity (recombinants).

C. Screening for HEV Recombinant Proteins

HEV convalescent antiserum was obtained from patients infected during documented HEV outbreaks in Mexico, Borneo, Pakistan, Somalia, and Burma. The sera were immunoreactive with VLPs in stool specimens from each of several other patients with ETNANB hepatitis.

A lawn of *E. coli* KM392 cells infected with about $10^4$ pfu of the phage stock from above is prepared on a 150 mm plate and incubated, inverted, for 15–18 hours at 37° C. The lawn is overlaid with a nitrocellulose sheet, causing transfer of expressed HEV recombinant protein from the plaques to the paper. The plate and filter are indexed for matching corresponding plate and filter positions.

The filter is washed twice in TBST buffer (10 mM Tris, pH 8.0, 150 mM NaCl, 0.05% Tween 20), blocked with AIB (TBST buffer with 1% gelatin), washed again in TBST, and incubated overnight after addition of antiserum (diluted to 1:50 in AIB, 12–15 ml/plate). The sheet is washed twice in TBST and then contacted with enzyme-labeled anti-human antibody to attach the labeled antibody at filter sites containing antigen recognized by the antiserum. After a final washing, the filter is developed in a substrate medium containing 33 ml NBT (50 mg/ml stock solution maintained at 4° C.) mixed with 16 ml BCIP (50 mg/ml stock solution maintained at 4° C.) in 5 ml of alkaline phosphatase buffer (100 mM Tris, 9.5, 100 mM NaCl, 5 mM MgC12). Purple color appeared at points of antigen production, as recognized by the antiserum.

D. Screening Plating

The areas of antigen production determined in the previous step are replated at about 100–200 pfu on an 82 mm plate. The above steps, beginning with a 15–18 hour incubation, through NBT-BCIP development, are repeated in order to plaque purify phase secreting an antigen capable of reacting with the HEV antibody. The identified plaques are picked and eluted in phage buffer (Maniatis, p. 443).

Two subclones which were selected are the 406.3-2 and 406.4-2 clones whose sequences are set forth above. These sequences were isolated from an amplified cDNA library derived from a human Mexico HEV stool specimen. Using the techniques described in this section, polypeptides expressed by these clones have been tested for immunoreactivity against a number of different human HEV-positive sera obtained from sources around the world. As shown in Table 4 below, 9 sera immunoreacted with the polypeptide expressed by the 406.4-2, and 8 sera immunoreacted with polypeptide expressed by the 406.3-2 clone.

For comparison, the Table also shows reactivity of the various human sera with the non structural peptide Y2. Only one of the sera reacted with the polypeptide expressed by this clone. No immunoreactivity was seen for normal expression products of the gt11 vector.

TABLE 4

Immunoreactivity of HEV Recombinant Proteins: Human Sera

| Sera | Source | Stage | 406.4-2(M) | 406.3-2(M) | 406.4-2(B) | 406.3-2(B) | Y2 | lgt11 |
|---|---|---|---|---|---|---|---|---|
| FVH-21 | Burma | A | – | – | NT | NT | – | – |
| FVH-8 | Burma | A | + | – | NT | NT | + | – |
| B-IgG | Burma | C | + | + | + | + | NT | – |
| SOM-19 | Somalia | A | + | + | + | + | – | – |
| SOM-20 | Somalia | A | + | + | + | + | – | – |
| IM-35 | Borneo | A | + | + | NT | NT | – | – |
| IM-36 | Borneo | A | – | – | NT | NT | – | – |
| PAK-1 | Pakistan | A | + | + | NT | NT | – | – |
| FFI-4 | Mexico | A | + | + | + | + | – | – |
| FFI-125 | Mexico | A | + | + | + | + | – | – |
| F387-C | Mexico | C | + | + | + | + | NT | – |
| Normal | U.S. | | – | – | – | – | – | – |

Y2 represents an amino acid sequence encoded by a 157 basepair nucleic acid sequence from the first open reading frame of the HEV genome.
Acute-phase sera are collected between 1 and 12 days after the onset of HEV-related symptoms.
Convalescent-phase sera are collected between 30 and 90 days after the onset of jaundice.
+, reaction; –, no reaction; NT, not tested; A, acute; C, convalescent.

E. Producing the 406.3-2(M) Antigen

The 406.3-2 gt11 plasmid from above is digested with EcoRI and the released HEV fragment is amplified by PCR in the presence of linkers which added an NcoI site at the 5' fragment end, and a BamHI site at the 3' fragment end. The amplified material is digested with NcoI and BamHI and inserted into the NcoI/BamHI site of the glutathione S-transferase vector pGEX™ expression vector, according to the manufacturer's instructions.

The pGEX™ plasmid is used to transform *E. coli* host cells, and cells which are successfully transformed with the pGEX™ vector are identified by immunofluorescence, using anti-HEV human antisera.

F. Producing the 406.4-2 Antigen

The 406.4-2 gt11 plasmid from above is digested with EcoRI and the released HEV fragment is amplified by PCR, and the amplified fragment is inserted into the NcoI/BamHI site of the pGEX™ expression vector, as above. Peptide expression of the 406.4-2 peptide is similar to that described for the 406.3-2 fusion peptide.

G. Producing the SG3 Antigen

The SG3 peptide is prepared by first amplifying the SEQ ID No. 7 sequence with 5' EcoRI-NcoI and 3' BamHI primer-linkers, using a gt10 phage BET1 clone plasmid containing the entire ORF2 and ORF3 regions of HEV (B). The amplified fragment is inserted into the EcoRI/BamHI site of a pBluescript™ vector (Stratagene, La Jolla, Calif.), according to the manufacturer's instructions. After vector propagation and harvesting, the cloned insert is released by digestion with NcoI and BamHI, and gel purified. The purified fragment is inserted into the NcoI/BamHI site of a pGEX™ vector, and expressed in an *E. coli* expression system. Peptide expression of the SG3 peptide is similar to that described for the 406.3-2 fusion peptide.

H. Producing the Capsid Protein

The capsid protein (B) is prepared substantially as described above by PCR amplification of the SEQ ID No. 1, from a pBET1 plasmid using a 5' primer containing an NcoI site and a 3' primer containing a BamHI site. The amplified fragment is inserted into the NcoI/BamHI site of a pGEX™ vector, and expressed in an *E. coli* expression system. The capsid protein (M) is similarly prepared.

I. Peptide Purification

HEV peptide antigens which are soluable, such as 406.4-2 and 406.3-2, are purified by polyacrylamide gel electrophoresis of bacterially expressed whole cell lysates. Crude lysate preparations are loaded on 7.5% SDS-PAGE gels and run until size markers corresponding to the predicted size of each protein have nearly run off each gel. The gel running buffer is replaced with fresh buffer and the gel is allowed to continue to run for 5 minute intervals. The gel running buffer is collected after each interval and replaced with fresh buffer. The fractions are dialyzed and concentrated, and each fraction tested for immunoreactivity to a pGEX™ fusion partner, glutathione S-transferase, specific monoclonal antibody. Highly reactive fractions are pooled.

Insoluble HEV peptides, such as SG3, are purified as follows. Cells induced to express the pGEX™ fusion protein are lysed with two passes through a french-press. The lysate is layered on a 40% solution of glycerol and spun at 3500 rpm in a J-20 rotor in a Beckman J221 centrifuge for 5 minutes. The pellet is resuspended in PBS then repelleted. The pellet is then resuspended in 6M urea, 6M guanadine in PBS pH 8.0 with homoginization for 5 minutes and repelleted. The suspension is filtered through a 0.22 um filter (Nalgene) and loaded on an IMAC column (Pharmacia) containing Fast Flow Chelating Sepharose™ (Pharmacia) loaded with 3 column volumes of a $CoCl_2$ solution according to the manufacturer's instructions. Elute the bound protein with a 2 column gradient of 6M urea, 6M guanadine, and between 0–1M imidizole in PBS with a pH range of 8.0 to 6.0. Strip with 0.1M EDTA in PBS and analyze fractions; e.g., by the ELISA protocol detailed in Example 4.

EXAMPLE 2

Human Primary Hepatocytes in Culture

A. Isolation of hepatocytes.

Hepatocytes were isolated from human liver obtained from Stanford University Medical Center. The liver was either perfused in situ or excised as a wedge for perfusion in laboratory. The initial perfusion was performed for 10 minutes at 60 ml/min using $Ca^{++}$-, $Mg^{++}$-free Hanks' balanced salt solution supplemented with 10 mM HEPES (pH7.4) and 0.5 mM [ethylene bis(oxyethylenenitrillo]-tetraacetic acid. Perfusion was continued for additional 20 minutes using Williams' medium E (WME) supplemented with 10 mM HEPES (pH7.4) and 100 U/ml collagenase (type I, Sigma Chemical Co., St. Louis, Mo.).

After perfusion the liver capsule was removed using fine forceps, and hepatocytes were dislodged by gentle shaking in collagenase solution. The hepatocyte suspension was filtered through several layers of gauze and mixed with an equal volume of WMW containing 10% fetal bovine serum (FBS). Hepatocytes were sedimented by centrifugation at 50 X g for 5 minutes and resuspended in WME containing 5% FBS. Hepatocytes were sedimented and resuspended in the manner for 2 additional times. The final cell preparation was further filtered through several layers of gauze before examining for viability using trypan blue. The cells were plated at a density of $2\times10^6$ cells per 60-mm Primaria plates (Falcon) pre-coated with collagen (Collaborative Research).

Cultures were incubated at 37° C. in 5% $CO_2$ for 3 hours to allow attachment and the medium was changed to a serum-free formulation and every 48 hrs thereafter. The serum-free formulation was a WME-based medium supplemented with growth factors, hormones, 10 mM HEPES (pH7.4), 100 ug/ml gentamicin, as has been described (Lanford, 1989).

B. Detection of Liver-Specific Proteins.

Human hepatocyte cultures were maintained in serum-free medium for various periods of time and labeled with [$^{35}$S]-methionine for 24 hrs. The medium was adjusted to contain 1 mM PMSF, 1 mM EDTA, and 1% NP40. Antibodies specific for the different plasma proteins were bound to protein A-agarose beads, the beads were washed with PBS, and aliquots of the labeled medium were incubated for 16 hrs at 4° C. with the antibody-bead complexes. The beads were washed 3 times with a buffer containing 1% NP40, and immunoprecipitated proteins were eluted with gel electrophoresis sample buffer containing 2% SDS and 2% 2-mercaptoethanol. Samples were analyzed by gradient SDS-PAGE (4 to 15%) and autoradiography.

EXAMPLE 3

In Vitro HEV Infection of Primary Human Hepatocytes

A. HEV Infection of human hepatocytes.

The HEV-infected cynomolgus monkey #73 stool pool (fourth passage) was used as an inoculum for infections of primary human hepatocytes. Various amounts of inoculum was diluted in 1 ml of serum-free medium (SFM) and applied to the culture during a 3 hr incubation period. This solution was then supplemented with 2 ml of fresh SFM and the entire mixture was incubated overnight. The next day, cell monolayers were washed with WME (10 mM HEPES, pH7.4) for three times and changed to fresh SFM, which was changed at two day intervals thereafter.

B. Immunofluorescence staining assay.

Primary cynomolgus monkey hepatocytes were isolated and plated in tissue culture plates with collagen-coated coverslips as described. Cells on coverslips were infected with either the HEV-infected cynomolgus monkey #73 stool pool or the NIH normal human serum three days after initial plating. The infections were allowed to proceed for 2 weeks.

Cells on coverslips were fixed in 90% acetone at room temperature for 1 minute. The coverslips were then air-dried. The coverslips were blocked in 1% goat serum in PBS for 1 hour, washed with PBS three times, and incubated with a mixture of rabbit antisera against HEV recombinant proteins 406.3-2(B), 406.4-2(M), and 406.4-2(B) at room temperature for 3 hours. The coverslips were again washed with PBS 3 times and reacted with fluorescein isothiocyanate-conjugated (FITC) goat anti-rabbit IgG(H+L) (Zymed) diluted in PBS-1% goat serum for 30 minutes. After the coverslips were washed with PBS for 3 times and air-dried, they were mounted with FITC glycerol solution and examined under a fluorescent microscope.

C. Reverse transcription/polymerase chain reaction (RT/PCR).

HEV infection of primary cynomolgus macaque hepatocytes was evaluated by RT/PCR assays. The primers for cDNA synthesis and PCR were based on the nucleotide sequences of the full-length HEV cDNA (A. Tam et al.). Primers HEV3.2SF1 (nt 6578–6597) and HEV3.2SF2 (nt 6650–6668) are of sense polarity from the ORF2 region of the viral genome and HEV3.2SR1 (nt 7108–7127) and HEV3.2SR2 (nt 7078–7097) are antisense primers within the region.

Following extraction of total cellular RNA from HEV-infected cells using one-step guanidinium procedure or HEV-infected supernatants according to the method of Chomczynski et al., aliquots of RNA samples were heat-denatured at 95° C. for 5 minutes and subjected to reverse transcription at room temperature for 5 minutes and 42° C. for 60 minutes using 200 units per reaction of MMLV-reverse transcriptase (BRL) in a 20 ul reaction volume containing 20 units of RNasin (Promega), 1x PCR buffer (Perkin-Elmer Cetus), with a concentration of 1 mM each deoxyribonucleotide (Perkin-Elmer Cetus), and 2.5 uM of HEV3.2SR1 primer. The reaction mixture was then heat-treated at 95° C. for 5 minutes to denature the MMLV-reverse transcriptase.

Ten microliters of the cDNA synthesis product was used for PCR in a final volume of 50 ul with 0.5 uM HEV3.2SF1 primer, 1.25 units Taq DNA polymerase (AmpliTaq, Perkin-elmer Cetus), and 1x PCR buffer, overlayed with 50 ul of mineral oil, and subjected to 40 cycles of PCR in a Perkin-Elmer thermocycler (95° C.×1 minute; 52° C.×2 minutes; 72° C.×30 seconds). Ten microliters of the first-round PCR product then underwent another 40 cycles of nested PCR (95° C.×1 minute; 55° C.×2 minutes; 72° C.×30 seconds) in a total volume of 50 ul containing the internal PCR primers HEV3.2SF2 and HEV3.2SR2.

First- and second-round PCR products were subjected to agarose electrophoresis, ethidium bromide stained and photographed under UV light. Southern transfer was performed and filters were hybridized with [$^{32}$P-dCTP]-labeled internal probe HEVORF2-7 exclusive of the primers (nt 6782–6997), and autoradiography performed.

EXAMPLE 4

Sensitivity of HEV ELISA

The HEV recombinant peptide SG3 is tested in combination with 406.3-2(B), 406.3-2(M), and 406.4-2(B) for immunoreactivity to IgG and IgM in human serum samples by ELISA as follows.

A. Serum Sources

The Saudi panel, provided by Dr. Purcell (National Institutes of Health), were specimens of sporadic cases of acute hepatitis within Saudi Arabia. All types of hepatitis cases were included in this panel. The Korean panel was from an in-house stored panel of sera collected from Seoul by Dr. Jungsuh Kim. The Pakistani panel, provided by Dr. John Ticehurst (University of Massachusettes), was from an outbreak of hepatitis among students within a housing unit in Abbottabbad in 1988. Sera in this panel was collected during acute hepatitis and early convalescence. All Pakistani cases were traced to fecal contamination of the water supply. All sera were tested under code with each of the four HEV antigens.

B. ELISA with HEV Peptide Antigens

The purified recombinant HEV peptides, 200 ng in 100 ul 0.05M sodium carbonate pH 9.5 (1.59 g $Na_2CO_3$, 2.93 g $NaHCO_3$, 0.02% sodium azide, pH 9.5, bring to 1000 ul), are pipetted into each well of a polystyrene microtitre plate. Plates are incubated at 37° C. for 1 hour. After overnight incubation at 4° C., the wells are washed in PBS-0.05% polyoxyethylene (20) monolaurate "Tween 20™" (Sigma) and blocked with 200 ul of 1% bovine serum albumin (BSA) in PBS for 1.5 hours at room temperature. The plates are rewashed with PBS-0.05% Tween 20™ and serum samples diluted 1:100 in antibody incubation buffer (10 mM Tris pH 7.5, 150 mM NaCl, 1% gelatin, 0.02% sodium azide) are added to incubate for 1 hour at room temperature. The wells are washed to remove any unbound 1st antibody and incubated for 1 hour at room temperature with 100 ul of 1 ug/ml of alkaline phosphatase conjugated goat anti-human IgG or IgM diluted in Antibody Diluent (1000 ml Tris buffered saline (40 mM Tris pH 7.5, 1M NaCl), 30 ml goat serum, 10 g bovine serum albumin, fraction V, 10 g non fat milk (Carnation), 1 g gelatin (EIA) grade, and 0.2 g thimersol (preservative), see Antibody Diluent Production, following). After final washing, 100 ul of alkaline phosphate substrate (Sigma) in diethanolamine buffer pH 9.8 (48.5 ml diethanolamine, $dH_2O$ to 500 ml, 50 mg $MgCl_2$, pH to 9.8, store in amber bottle) was added at room temperature for 30 minutes. The plates are read at an absorbance of 405 nm. A serum positive for anti-HEV antibodies will have an ELISA signal greater than 3-fold the signal generated with non-recombinant glutathione-S-transferase protein (pGEX fusion partner). The results are shown in Table 1.

C. Antibody Diluent Production

Antibody Diluent is made as follows: Heat 200 ml of TBS to 60° C. and melt gelatin. Bring to 1000 ml with TBS. Add BSA when the temperature has cooled to 40° C. Stir at room temperature until BSA is in solution, then add the goat serum. Add thimeresol. Reagent can be stored for two weeks at 4° C. Stir milk in at room temperature for 30 minutes, 30 minutes prior to use.

EXAMPLE 5

Testing Human Sera by ELISA for Immunoreactivity to HEV Peptides

The sera in this assay is a subset of all sera in the Pakistani panel (described in Example 4) and is limited to cases of non-A, non-B hepatitis through serological testing (with commercially available kits) and by RT-PCR (as described in A following) or clear clinical symptoms of hepatitis; e.g., liver inflamation and jaundice.

A. PCR Confirmatory Assay for HEV Infection

The first round of amplification is done with a sense primer from nucleotides 6581 to 6600 and an antisense primer from nucleotides 7111 to 7130 for 35 cycles. The reaction conditions are 1 minute 20 seconds at 94° C., 2 min. at 60° C., and 3 min. at 72° C., followed by a 7 min. extension at 72° C. Nested PCR is done with the same conditions using a sense primer from nucleotides 6663 to 6671 and an antisense primer from nucleotides 7081 to 7100. Samples are analyzed by agarose gel electrophoresis and Southern blot hybridization using a radiolabeled probe spanning nucleotides 6785 to 6804. Only samples taken from individuals with confirmed HEV infection at acute infection are used in the following assay.

B. SG3 Antigen Sensitivity for Detecting Anti-HEV

Peptides SG3, 406.3-2(M), 406.4-2(B), and 406.4-2(M) are coated individually onto wells of polystyrene 96-well microtitre plates and ELISAs are performed with confirmed HEV-positive sera identically as in Example 4, above. The results are listed in Table 2.

EXAMPLE 6

Specificity of HEV Peptides

Sera from the U.S. (California and Texas) and the Middle East (Saudi panel described in Example 4) which assayed positive for HAV, HBV, or HCV with commercially available serologically based test kits, is used to determine whether peptides SG3, 406.3-2(M), 406.4-2(B), and 406.4-2(M) are cross reactive with antisera to these hepatitis viruses. The peptides are co-coated onto polystyrene 96-well microtitre plates and ELISA's are performed as in Example 4. The results are listed in Table 3.

While the invention has been described with reference to particular embodiments, methods, construction and use, it will be apparent to those skilled in the art that various changes and modifications can be made without departing from the invention. For example, short peptides spanning only the immunoreactive region(s) contained in the larger peptides described herein can be substituted for the larger peptides in the methods and kits described and claimed.

It is claimed:

1. A method of detecting hepatitis E virus (HEV) antibodies in an individual, comprising providing a peptide antigen having a sequence selected from the group consisting of SEQ ID NO:13 and SEQ ID NO:14, and internally consistent variations between SEQ ID NOS:13 and 14, reacting a serum sample taken from the individual with the peptide, and examining the peptide for the presence of bound antibodies, where the presence of bound antibodies indicates the presence of HEV antibodies in said individual.

2. The method of claim 1, wherein the peptide provided is attached to a solid support, said reacting includes contacting such serum with the support and said examining includes reacting the support and bound antibodies with reporter-labeled anti-human antibodies.

3. The method of claim 1, wherein a second peptide antigen is provided having an amino acid sequence selected from the group consisting of SEQ ID NO:11 and SEQ ID NO:12, and internally consistent variations between SEQ ID NOS:11 and 12, said reacting includes reacting the serum sample taken from the individual with both peptide antigens, and said examining includes examining both peptide antigens for the presence of bound antibodies.

4. The method of claim 1, wherein a second peptide antigen is provided having an amino acid sequence selected from the group consisting of SEQ ID NO:17 and SEQ ID NO:18, and internally consistent variations between SEQ ID NOS:17 and 18, said reacting includes reacting the serum sample taken from the individual with both peptide antigens, and said examining includes examining both peptide antigens for the presence of bound antibodies.

5. A kit for ascertaining the presence of antibodies to hepatitis E virus in a serum sample taken from an individual, comprising a solid support with surface-bound peptide antigen having a sequence selected from the group consisting of SEQ ID NO:13 and SEQ ID NO:14, and internally consistent variations between SEQ ID NOS:13 and 14.

6. The kit of claim 5, wherein the solid support has a second surface-bound peptide antigen having an amino acid sequence selected from the group consisting of SEQ ID N0:11 and SEQ ID NO:12, and internally consistent variations between SEQ ID NOS:11 and 12.

7. The kit of claim 5, wherein the solid support has a second surface-bound peptide antigen having an amino acid sequence selected from the group consisting of SEQ ID NO:17 and SEQ ID NO:18, and internally consistent variations between SEQ ID NOS:17 and 18.

8. A method of detecting hepatitis E virus (HEV) antibodies in an individual, comprising providing a peptide antigen having a sequence selected from the group consisting of SEQ ID NO:11 and SEQ ID NO:12, and internally consistent variations between SEQ ID NOS:11 and 12, reacting a serum sample taken from the individual with the peptide, and examining the peptide for the presence of bound antibodies, where the presence of bound antibodies indicates the presence of HEV antibodies in said individual.

9. The method of claim 8, wherein the peptide provided is attached to a solid support, said reacting includes contacting such serum with the support and said examining includes reacting the support and bound antibodies with reporter-labeled anti-human antibodies.

10. The method of claim 8, wherein a second peptide antigen is provided having an amino acid sequence selected from the group consisting of SEQ ID NO:17 and SEQ ID NO:18, and internally consistent variations between SEQ ID NOS:17 and 18, said reacting includes reacting the serum sample taken from the individual with both peptide antigens, and said examining includes examining both peptide antigens for the presence of bound antibodies.

11. A kit for ascertaining the presence of antibodies to hepatitis E virus in a serum sample taken from an individual, comprising a solid support with surface-bound peptide antigen having a sequence selected from the group consisting of SEQ ID NO:11 and SEQ ID NO:12, and internally consistent variations between SEQ ID NOS:11 and 12.

12. The kit of claim 11, wherein the solid support has a second surface-bound peptide antigen having an amino acid sequence selected from the group consisting of SEQ ID NO:17 and SEQ ID NO:18, and internally consistent variations between SEQ ID NOS:17 and 18.

* * * * *

UNITED STATES PATENT AND TRADEMARK OFFICE

CERTIFICATE OF CORRECTION

PATENT NO. : 5,686,239

DATED : Nov. 11, 1997

INVENTOR(S) : G.R. Reyes, et al.

It is certified that error appears in the above-indentified patent and that said Letters Patent is hereby corrected as shown below:

Column 1, line 21 insert --The U.S. Government has a nonexclusive, nontransferable, irrevocable paid-up license to practice or have practiced this invention for or on its behalf as provided for by the terms of Contract DAMD17-90-C-0092 awarded by the U.S. Department of the Army.--

Signed and Sealed this

Twenty-fourth Day of November, 1998

Attest:

BRUCE LEHMAN

Attesting Officer

*Commissioner of Patents and Trademarks*